(12) United States Patent
Nishikubo

(10) Patent No.: US 8,905,934 B2
(45) Date of Patent: Dec. 9, 2014

(54) ULTRASOUND TRANSDUCER, ULTRASOUND PROBE, AND ULTRASOUND DIAGNOSTIC APPARATUS

(75) Inventor: Yuichi Nishikubo, Kanagawa (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 228 days.

(21) Appl. No.: 13/607,039

(22) Filed: Sep. 7, 2012

(65) Prior Publication Data

US 2013/0085390 A1  Apr. 4, 2013

(30) Foreign Application Priority Data

Sep. 30, 2011  (JP) .................................. 2011-216053

(51) Int. Cl.
*A61B 8/14*  (2006.01)
*H01L 41/083*  (2006.01)
*H01L 41/257*  (2013.01)
*A61B 8/00*  (2006.01)
*H01L 41/18*  (2006.01)
*H01L 41/187*  (2006.01)
*H01L 41/193*  (2006.01)

(52) U.S. Cl.
CPC ............ *H01L 41/083* (2013.01); *H01L 41/257* (2013.01); *A61B 8/4483* (2013.01); *H01L 41/183* (2013.01); *H01L 41/187* (2013.01); *H01L 41/193* (2013.01)
USPC ........... 600/459; 600/437; 600/443; 310/357; 310/359; 310/366

(58) Field of Classification Search
None
See application file for complete search history.

(56) References Cited

U.S. PATENT DOCUMENTS 5,034,649 A * 7/1991 Chida et al. .................... 310/332
5,381,067 A * 1/1995 Greenstein et al. ............ 310/334

FOREIGN PATENT DOCUMENTS

JP  2002-011004  1/2002
JP  2004-208918  7/2004

* cited by examiner

*Primary Examiner* — Long V. Le
*Assistant Examiner* — Farshad Negarestan
(74) *Attorney, Agent, or Firm* — Lucas & Mercanti, LLP

(57) ABSTRACT

Object is that an output sound pressure at transmission or an output voltage at reception of a predetermined higher resonance component becomes higher than those of the primary resonance component. The piezoelectric material layer 24 has an electrode on the surface of the piezoelectric material of between the layer and both ends, and outputs and inputs an electrical signal with this electrode. The piezoelectric material 24 has a remanent polarization in a thickness direction, the relationship of the (4P+1)th layer piezoelectric material from fixed end side is used as the basic relationship, piezoelectric materials are periodically arranged so that piezoelectric materials of (4p+2)th and (4p+3)th layer each has an opposite relationship, and (4p+4)th layer has the same relationship as the basic relationship. On the fixed-end side of the piezoelectric material layer 24, provided is the de-matching layer 23 with larger acoustic impedance than the piezoelectric material layer 24 for reflecting vibration propagated from the piezoelectric material layer 24 to the fixed-end side.

11 Claims, 30 Drawing Sheets

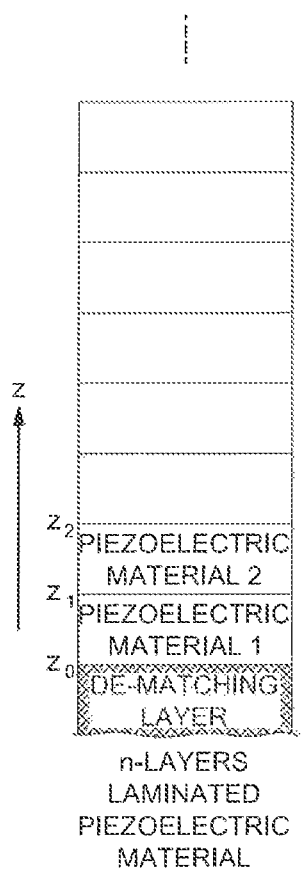
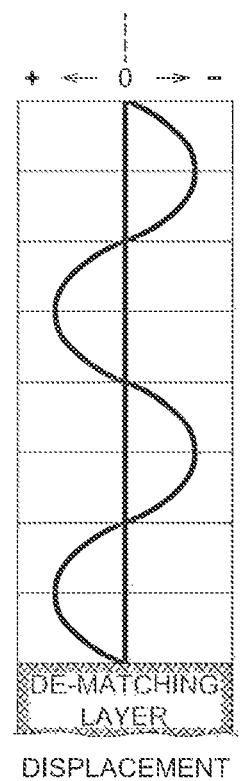
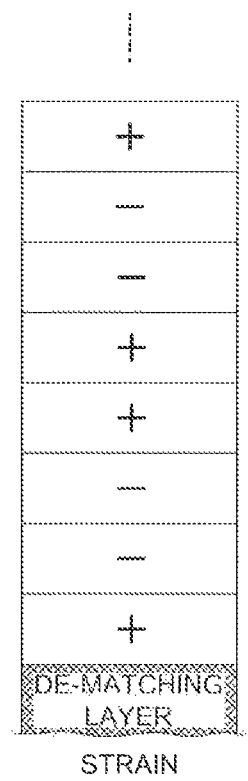
FIG. 7a
n-LAYERS LAMINATED PIEZOELECTRIC MATERIAL
FIG. 7b
DISPLACEMENT
FIG. 7c
STRAIN

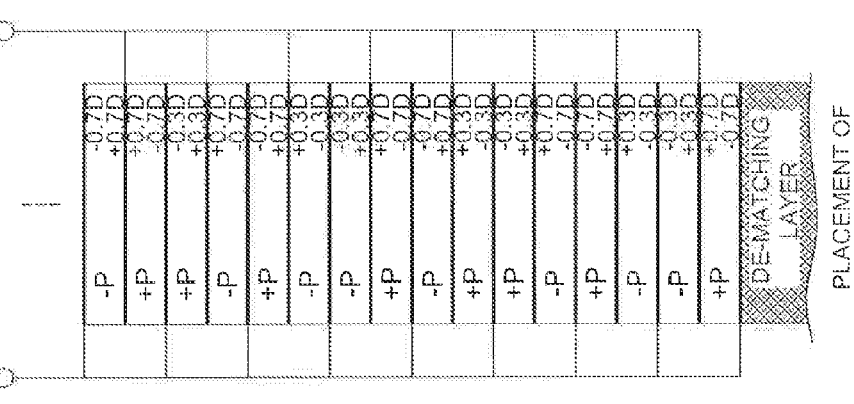
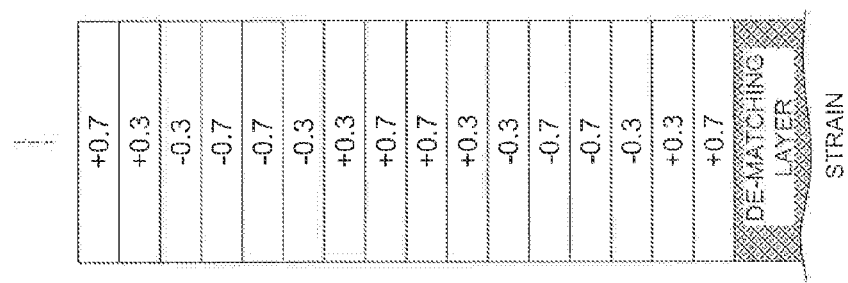
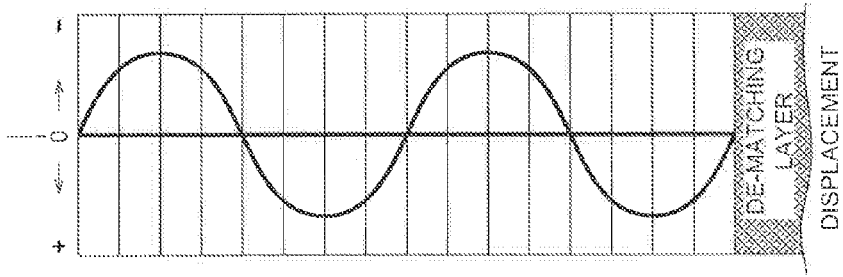
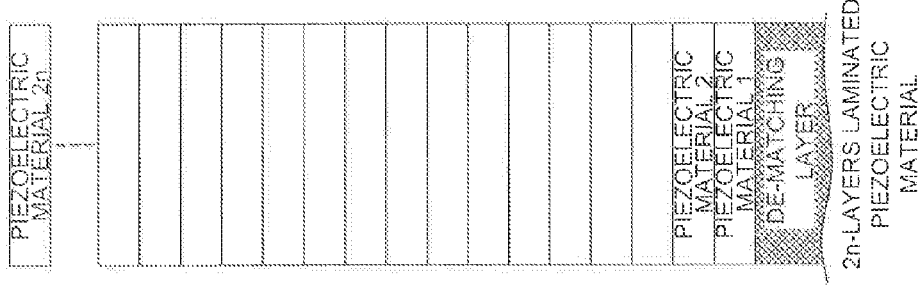

FIG. 10
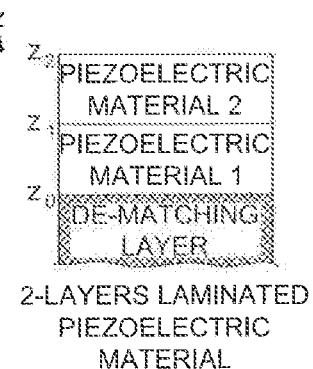
2-LAYERS LAMINATED
PIEZOELECTRIC
MATERIAL
FIG. 11a  FIG. 11b
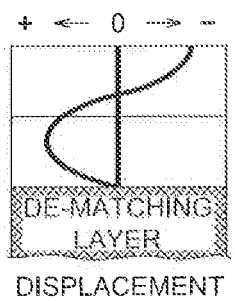
DISPLACEMENT
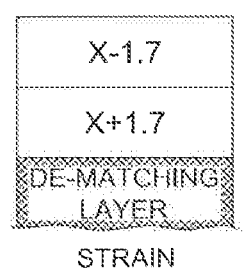
STRAIN
FIG. 12
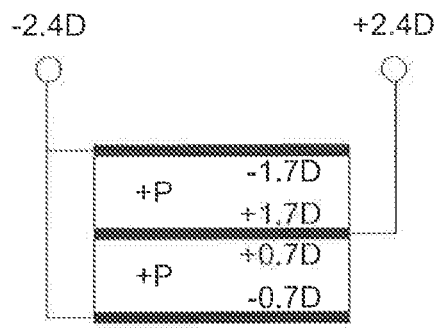

3-LAYERS LAMINATED
PIEZOELECTRIC
MATERIAL

DISPLACEMENT

STRAIN

6-LAYERS LAMINATED PIEZOELECTRIC MATERIAL

DISPLACEMENT

STRAIN

FIG. 27

| | THICKNESS [μm] | MATERIAL CONSTITUTION | | CONTENT OF FILLER [wt%] | SOUND SPEED [m/s] | SPECIFIC GRAVITY [g/cm³] | ACOUSTIC IMPEDANCE [Mrayl.] |
|---|---|---|---|---|---|---|---|
| | | BASE MATERIAL | FILLER | | | | |
| UPPERMOST LAYER | 10 | *1 | Zinc oxide | 40 | 900 | 1.45 | 1.3 |
| 2ND LAYER | 10 | EVA | None | 0 | 2000 | 0.9 | 1.8 |
| 3RD LAYER | 10 | EP007 (produced by CEMEDINE Co.,Ltd) | None | 0 | 2300 | 1.1 | 2.5 |
| 4TH LAYER | 10 | C-1001A/B (produced by TESK Co.,Ltd) | None | 0 | 2500 | 1.2 | 3.0 |
| LOWERMOST LAYER | 10 | C-1001A/B (produced by TESK Co.,Ltd) | Tungsten trioxide | 15 | 2300 | 1.5 | 3.5 |

*1: YE5822 (produced by Momentive Performance Materials Inc.)

ULTRASOUND TRANSDUCER, ULTRASOUND PROBE, AND ULTRASOUND DIAGNOSTIC APPARATUS

This application is based on Japanese Patent Application No. 2011-216053 filed on Sep. 30, 2011 in Japan Patent Office, the entire content of which is hereby incorporated by reference.

FIELD OF THE INVENTION

The present invention relates to an ultrasound transducer, an ultrasound probe, and ultrasound diagnostic imaging apparatus.

TECHNICAL BACKGROUND

Generally a piezoelectric material is used for an ultrasound transducer (ultrasonic transducer), since the piezoelectric material has a function to transform kinetic energy into electric energy or vice versa, what is called as a binding action between electrical system and mechanical system. Used piezoelectric material has the shape of a sheet, tabular or cylindrical having a pair of electrode in which one electrode is feed to a back layer, and another electrode contacts to a medium through an acoustic lens or a matching layer.

Most of piezoelectric ultrasound transducers emit a sound wave to a medium by $d_{33}$ mode or $e_{33}$ mode, or detect the sound wave which propagates to medium $d_{33}$ mode is generally said to be as a longitudinal oscillation of a pillar-shaped transducer, and $e_{33}$ mode is as thickness vibration of a plate type transducer. In ferroelectrics, such as PZT (lead zirconate titanate) ceramics and PVDF (polyvinylidene fluoride), high-dielectrics such as P(VDCN/VAc) (vinylidene cyanide-vinylacetate copolymer), and a porous polymer electret piezoelectric material, remanent polarization is kept according to the orientation of the electric dipole by polling processing, and $d_{33}$ and $e_{33}$ are shown. On the other hand, with respect to a piezoelectric crystal without remanent polarization, C axis in the case of a piezoelectric crystal such as ZnO (zinc oxide), LiNbO3 (lithium niobate single crystal) and KNbO3 (potassium niobate single crystal), and A axis in the case of rock crystal is perpendicularly orientated against an electrode surface respectively, whereby $d_{33}$ or $e_{33}$ (in case of rock crystal, $d_{11}$ or $e_{11}$) are shown. In the case of a piezoelectric composite material, it depends on a used material.

Here, in the piezoelectric material which constitutes an ultrasound transducer, the simplest dynamic boundary condition is a case where one end is a fixed end and another end is a free end. Theoretically, there is a relationship between an acoustic impedance Z (unit is MRayl.) of a touched body and a boundary condition that Z=0 for the free end and Z=∞ for the fixed end. However, in the present specification, it is not so strictly defined as such. When an impedance Z of a piezoelectric material except for an adhesive layer and an electrode layer is small or equal to an impedance Z of a touched body, it shall be regarded as a fixed end, and when large, it shall be regarded as a free end. Moreover, a resonance of the longitudinal oscillation or thickness vibration of a piezoelectric material is used for wave transmission and wave reception of art ultrasound transducer. The resonance frequency fr is mainly decided by physical properties and dimension of a piezoelectric material, although it depends on a structure of a transducer or how to press against a medium. Therefore, in this specification, factors are eliminated which are other than the physical properties or the dimension of a piezoelectric material and affect change in resonance frequency.

The resonance frequency fr in $d_{33}$ mode or $e_{33}$ mode of a piezoelectric material is represented by the following Expression (1) from the sound velocity v of a piezoelectric material and height (thickness) h.

$$fr=v/4h \quad (1)$$

Generally this is called λ/4 resonance. λ means a wavelength inside of the piezoelectric material. In addition, there is λ/2 resonance in which both ends are freed. The resonance frequency of λ/2 resonance is as twice as that of λ/4 resonance.

On the other hand, the sound velocity v of the above-mentioned piezoelectric material is represented by the following Expression (2) for the longitudinal oscillation of a pillar-shaped transducer, and the following Expression (3) for the thickness vibration of the plate type transducer. Herein, s represents elastic compliance, c represents elastic stiffness and ρ represents density.

$$v=(1/s\rho)^{1/2} \quad (2).$$

$$v=(c/\rho)^{1/2} \quad (3)$$

It is understood from above-mentioned Expressions (1)-(3) that the transmission frequency and reception frequency of a transducer are mainly determined with height (thickness) h, elastic modulus s and density ρ of piezoelectric material.

It is required for the ultrasound diagnostic imaging apparatus used for a medical field to perform a high frequency of a transducer or to improve in a wave transmission-and-reception performance in order to obtain an image having a high resolution. In order to improve the wave transmission-and-reception performance in the ultrasound transducer using a piezoelectric material, it is an important factor for transmitting an electrical signal by a high S/N ratio to match electric impedances between a transducer and an electric processing circuit. Moreover, since a transmission-and-reception frequency is determined by a thickness of the piezoelectric material, it is necessary to make the piezoelectric material thinner for perforating a high frequency. A thinner piezoelectric material contributes to lower electrical impedance and to have, an advantage to an impedance matching with an electric circuit. However, the range of the reduction of this electrical impedance is at most an inverse of a thickness ratio. Moreover, the thinner piezoelectric material makes a manufacturing process difficult such as thickness control, or handling.

In the conventional technology, it is used a higher resonance component in the transmission-and-reception wave signal of the conventional λ/4 resonance transducer in order to obtain a high frequency signal. However, sensitivity of higher resonance component is weaker compared with a primary resonance component, and is easy to decrease by dumping of a piezoelectric material or circumference material, whereby there is problem that it is hardly to obtain the signal with a high S/N ratio. Here, with reference to FIG. 1, $e_{33}$ thickness stretch mode will be explained as an example of the transmission-and-reception wave of the ultrasound using higher resonance mode. This FIG. 1 and the following explanation are shown in the Non-patent Document 1. Constants of the elements which constitute the equivalent circuit of this FIG. 1 are as follows:

$$C_n = p_n k_t^2 C_0 \quad (4)$$

$$L = 1/\omega_{pi}^2 C_1 \quad (5)$$

$$p_n = (1/n^2)(8/\pi^2), n=2m-1 \quad (6),$$

wherein $C_n$ represents a capacitance of each element, L represents an inductance, $k_t$ represents an electromechanical coupling coefficient in thickness stretch mode and $\omega_{pi}$ represents a resonance frequency.

When approximated with $p_n \approx 1/n^2$ in the above-mentioned Expression (6), Expression (4) will be:

$$C_n/C_0 = k_t^2/n^2 \qquad (7).$$

Expression (7) shows that the effective value of the electromechanical coupling coefficient in the n-th higher resonance mode decreases to 1/n. Since it is n=1 in the case of the primary resonance-mode, Expression (7) will be:

$$C_{n=1}/C_0 = k_t^2 \qquad (8).$$

This Expression coincides with Expression (9) showing a relational expression of $k_t$ and dielectric constant in the primary resonance mode:

$$\in^T/\in^S = 1 + k_t^2 \qquad (9),$$

wherein $\in^T$ and $\in^S$ are set as $\in^T = C_0 + C_n$, $\in^S = C_0$; and $\in^S$ represents a dielectric constant of bound conditions, $\in^T$ represents a dielectric constant of free conditions, and $C_0$ and $C_n$ each represents electric capacitance. To $d_{33}$ mode, the above-mentioned Expression (4) is replaced to the following Expression:

$$C_n = p_n(k_{33}^2/1-k_{33}^2)C_0 \qquad (10),$$

and the same result will be obtained.

When the 3rd resonance component is transmitted and received, an effective value of the electromechanical coupling coefficient is given by Expression (7) using n=3. When an apparent coupling coefficient is set with $k_t'$, $k_t' = k_t/n = k_t/3$. This result means that the apparent coupling coefficient declines to ⅓, when the 3rd resonance component is transmitted and received.

FIG. 2 is the graph which shows the frequency characteristic (calculated value) of the complex dielectric constant of the piezoelectric material which shows the primary resonance mode of thickness resonance at 1 MHz. Herein, $k_t=0.3$, $h/2v=2.485\times10^{-7}$ (s) and $\tan \delta_m=0.04$.

The maximum and the minimum of the real part (referred to as a referential mark α1) and the maximum of an imaginary part (referred to as a referential mark α2) shown at 1 MHz are based on the primary resonance component of thickness resonance. Further, the 3rd resonance component is shown at 3 MHz, and the 5th resonance component at 5 MHz. On the other hand, when the 3rd resonance component shown in FIG. 2 is applied to a piezoelectric material model which has the primary resonance component at 3 MHz, it coincides with a case in which a coupling coefficient and thickness of the piezoelectric material are set to ⅓ as shown in FIG. 3. These results are in agreement with the above-mentioned interpretation. FIG. 3 is a graph which shows the frequency characteristic (calculated value) of the complex dielectric constant of the piezoelectric material which shows a thickness resonance. Herein, a dashed line is the case of $k_t=0.3$, $h/2v=2.485\times10^{-7}$ (s) and $\tan \delta_m=0.04$ as mentioned above. On the other hand, a solid line is a case of $k_t=0.1$, $h/2v=8.300\times10^{-7}$ (s) and $\tan \delta_m=0.04$.

As mentioned above, the problems of the conventional technology are that an apparent electromechanical coupling coefficient decreases to 1/n when detects n-th resonance component, and that an electrical impedance is unambiguously decided by the dimension of a piezoelectric material.

On the other hand, in an ultrasound diagnostic apparatus for medical application, Tissue Harmonic Imaging (THI) diagnosis using a harmonic signal occurred in a living body is becoming a standard diagnostic modality in view of obtaining a clear diagnostic image which can not be obtained by the conventional B mode diagnosis. When the used frequency becomes high such as Harmonic Imaging, there are many advantages such that a side lobe level becomes small, S/N and a contrast resolution becomes good, and a beam width becomes thin and azimuthal resolution becomes good, and since sound pressure is still smaller at close range and change of sound pressure is little, whereby multiple reflection does not happen.

In Patent Document 1, proposed is an ultrasound diagnostic apparatus in which a signal received by each piezoelectric element of the ultrasound transducer is added by the phasing summing circuit, input commonly to a filter of a fundamental-wave band, and a filter of a harmonics band, weighted to those outputs by gain respectively corresponding to the depth of the diagnosing area of a test object, and compounded, whereby attenuation of the harmonic component in a deep diagnosing area is interpolated by the fundamental wave. That is, in reception of harmonics, the fall of the above-mentioned electromechanical coupling coefficient is compensated by using a filter and an amplifier.

Similarly, in Patent Document 2, proposed is an ultrasound diagnostic imaging apparatus in which the piezoelectric element for harmonics is laminated to the piezoelectric element for the fundamental waves, and an ultrasound for transmission is emitted from the piezoelectric element with the fundamental frequency. On a signal component received by the piezoelectric element for these fundamental wave, a plurality of harmonic components received by the piezoelectric elements for harmonics and a desired component extracted by passing bandpass filter respectively are summed by adjusting gain individually, whereby the ultrasound diagnostic imaging apparatus which acquired the signal according to the depth of the diagnosing area.

PRIOR TECHNICAL DOCUMENT

Patent Document

Patent Document 1: Unexamined Japanese Patent Application Publication (hereinafter referred to as JP-A) No. 2002-11004

Patent Document 2: Examined Japanese Patent Application Publication No. 4192598

Non-Patent Document

Non-patent Document 1: Takurou Ishida, Atsudenzai Kagaku no Kiso (Basic science of piezoelectric materials), Ohm sha

SUMMARY

However, in the above-mentioned conventional technology, it is necessary to intercalate filters or amplifiers in the signal paths from a plurality of piezoelectric elements.

An object of the present invention is to provide an ultrasound transducer, an ultrasound probe, and an ultrasound diagnostic imaging apparatus which can exhibit an output sound pressure at the time of transmission of a required higher resonance component or the an output voltage at the time of reception larger than those of the primary resonance component.

In order to achieve at least one object mentioned above, according to a first aspect of the present invention, there is provided an ultrasound transducer that comprises a laminated piezoelectric material in which n-layer piezoelectric materials (n is an integer of 3 or more) each having an equal thickness are laminated and comprises electrodes between the piezoelectric material layers and on both end surfaces of the laminated piezoelectric material for input and output of an electrical signal, wherein the ultrasound transducer resonates by a thickness stretch of the piezoelectric materials, the piezoelectric material layer each has a remanent polarization in a thickness direction, a de-matching layer is provided on an opposite surface side of a transmission of an ultrasound which has a larger acoustic impedance than the laminated piezoelectric material and reflects a vibration propagated from the laminated piezoelectric material to the de-matching layer side, and provided that a relationship between a direction of an electrical displacement by the direct piezoelectric effect or a direction of an electrical field of a piezoelectric material generated by a voltage applied to the electrode and a direction of the remanent polarization in the (4P+1)th layer from the de-matching layer side (P is 0 or a positive integer) is a basic relationship, piezoelectric material layers are periodically arranged so that (4P+2)th layer of the piezoelectric materials adjacent to (4P+1)th layer and (4P+3)th layer thereon each has an opposite relationship to the basic relationship, and (4P+4)th layer has the same relationship as the basic relationship.

According to a second aspect of the present invention, there is provided an ultrasound transducer that comprises a laminated piezoelectric material in which n-layers of piezoelectric materials (n is an integer of 3 or more) each having an equal thickness are laminated and comprises electrodes between the piezoelectric material layers and on both end surfaces of the laminated piezoelectric material for input and output of an electrical signal, wherein the ultrasound transducer resonates by a thickness stretch of the piezoelectric materials, the piezoelectric material each has a remanent polarization in a thickness direction, a de-matching layer is provided on an opposite surface side of a transmission of an ultrasound which has a larger acoustic impedance than the laminated piezoelectric material and reflects a vibration propagated from the laminated piezoelectric material to the de-matching layer side, and provided that a relationship between a direction of an electrical displacement by the direct piezoelectric effect or a direction of an electrical field of a piezoelectric material generated by a voltage applied to the electrode and a direction of the remanent polarization in the (8P+1)th layer from the de-matching layer side (P is 0 or a positive integer) is a basic relationship, piezoelectric materials are periodically arranged so that (8P+2)th layer of the piezoelectric materials adjacent to (8P+1)th layer has the same relationship as the basic relationship, (4P+3)th layer to (8P+6)th layer thereon each has an opposite relationship to the basic relationship, and (8P+7)th layer and (8P+8)th layer each has the same relationship as the basic relationship.

According to a third aspect of the present invention, there is provided the ultrasound transducer of the first or the second aspect, wherein a plurality of the piezoelectric material layers are in an electrically parallel connection each other mutually by connecting two electrodes each located at outermost side of two adjacent piezoelectric material layers.

According to a fourth aspect of the present invention, there is provided an ultrasound transducer of any one of the first to the third aspect that comprises a laminated piezoelectric material which comprises 3×m layers of piezoelectric materials (m is an integer of 1 or more).

According to a fifth aspect of the present invention, there is provided the ultrasound transducer of any one of the first to the fourth aspect, wherein the de-matching layer comprises a tungsten carbide.

According to a sixth aspect of the present invention, there is provided an ultrasound probe that comprises die ultrasound transducer of any one of the first to the fifth aspect, and outputting an ultrasound by inputting an electrical signal into the laminated piezoelectric material through the electrodes.

According to a seventh aspect of the present invention, there is provided an ultrasound probe that comprises the ultrasound transducer of any one of the first to the fifth aspect, wherein the laminated piezoelectric material receives an ultrasound and changes into an electrical signal, and outputs the electrical signal through the electrode.

According to an eighth aspect of the present invention, there is provided the ultrasound probe of the seventh aspect, which outputs an ultrasound by inputting an electrical signal into the laminated piezoelectric material through the electrode.

According to a ninth aspect of the present invention, there is provided the ultrasound probe of any one of the sixth to the eighth aspect that comprises a plurality of the ultrasound transducers formed in array by forming electrode arranged in array with a sequence at a predetermined interval on the surface of the piezoelectric material.

According to a tenth aspect of the present invention, there is provided the ultrasound probe of any one of the sixth to the ninth aspect comprising a circuit board which connects with the electrode electrically and has a predetermined wiring pattern, and the laminated piezoelectric material is integrally attached to the circuit board.

According to an eleventh aspect of the present invention, there is provided an ultrasound diagnostic imaging apparatus that comprises the ultrasound probe of the seventh or the eighth aspect, a reception unit which receives the electrical signal changed in the ultrasound probe as a received signal, an image processing unit which generates an ultrasound image data based on the received signal received by the reception unit.

According to the present invention, an output sound pressure at the time of transmission of a required higher resonance component or an output voltage at the time of reception can be larger than those of the primary resonance component.

BRIEF DESCRIPTION OF THE DRAWING

FIGS. 7a, 7b and 7c are schematic figures showing a displacement and a strain at the time of the n-layer piezoelectric transducer of FIG. 6 in case of exciting or detecting the n-th resonance component.

FIGS. 9a, 9b, 9c and 9d are schematic figures showing the structure of 2n-layer piezoelectric transducer for detecting the n-th resonance component.

FIG. 10 is a detailed Example according to the view of the present invention shown by FIG. 8, and is a schematic sectional drawing showing the structure of a 2-layer piezoelectric transducer.

FIGS. 11a and 11b are figures for explaining displacement and a strain at the time of transmission-and-reception of the higher resonance component in the 2-layer piezoelectric transducer of FIG. 10.

FIG. 12 is a figure showing the relationship between direction of the remanent polarization of each piezoelectric material and the electric displacement by the direct piezoelectric effect at the time of detecting the 3rd resonance component in a 2-layer piezoelectric transducer of FIGS. 10, 11a and 11b.

FIG. 27 is a figure explaining the composition of an acoustic matching layer.

PREFERRED EMBODIMENT OF THE INVENTION

At first a concept of the ultrasound transducer used for ultrasound diagnostic imaging apparatus for the medical application of the present invention will be described. The inventor of the present invention found that the 3rd or higher resonance mode component can be efficiently transmitted and receipted by laminating the piezoelectric materials having the same thickness according to a certain rule. The ultrasound transducer of the present invention comprises the laminated piezoelectric material which is constituted based on the above knowledge of the inventor of the present invention. Hitherto, many techniques of laminating the piezoelectric material have been reported, however the present invention focuses on that strain distribution exists in the piezoelectric material during the transmission-and-reception of the above-mentioned 3rd or higher resonance mode component.

Figure 1:
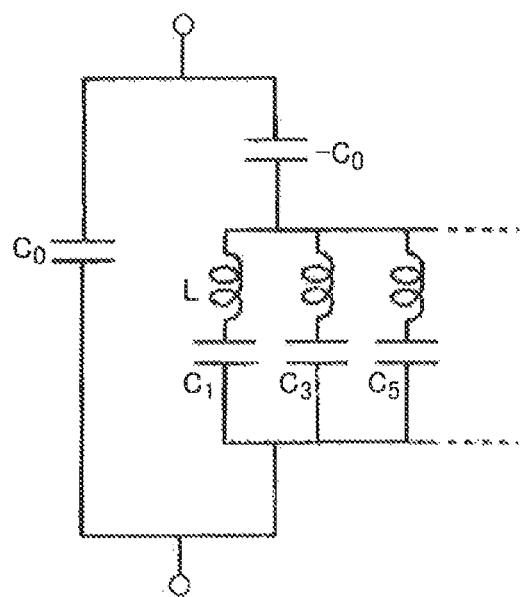
FIG. 1 is a figure showing an equivalent circuit in the thickness stretch mode of piezoelectric material.
Figure 2:
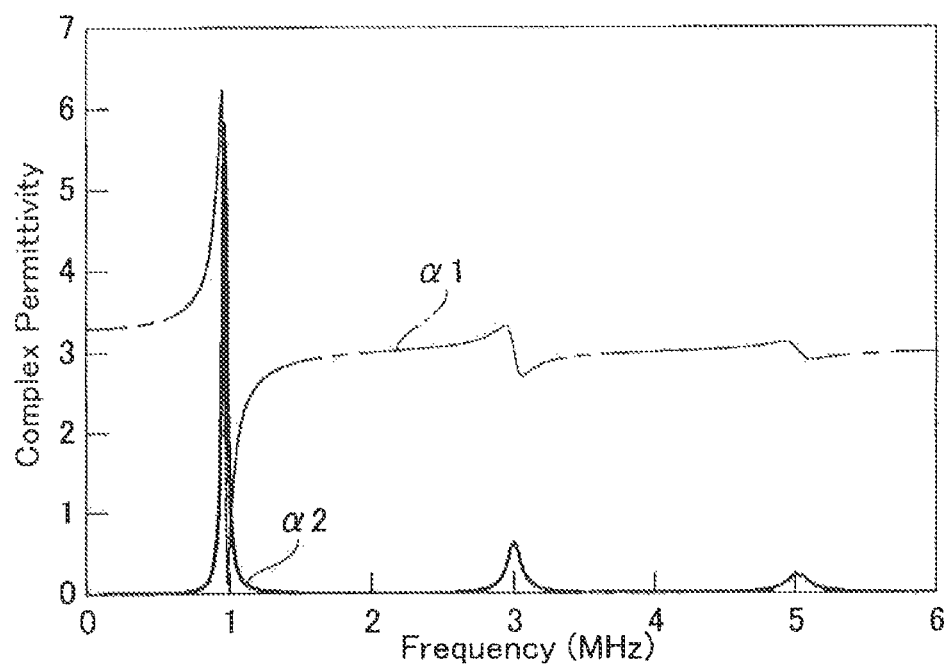
FIG. 2 is a graph showing a frequency characteristic of the complex dielectric constant of the piezoelectric material which has the primary resonance mode of thickness resonance at 1 MHz.
Figure 3:
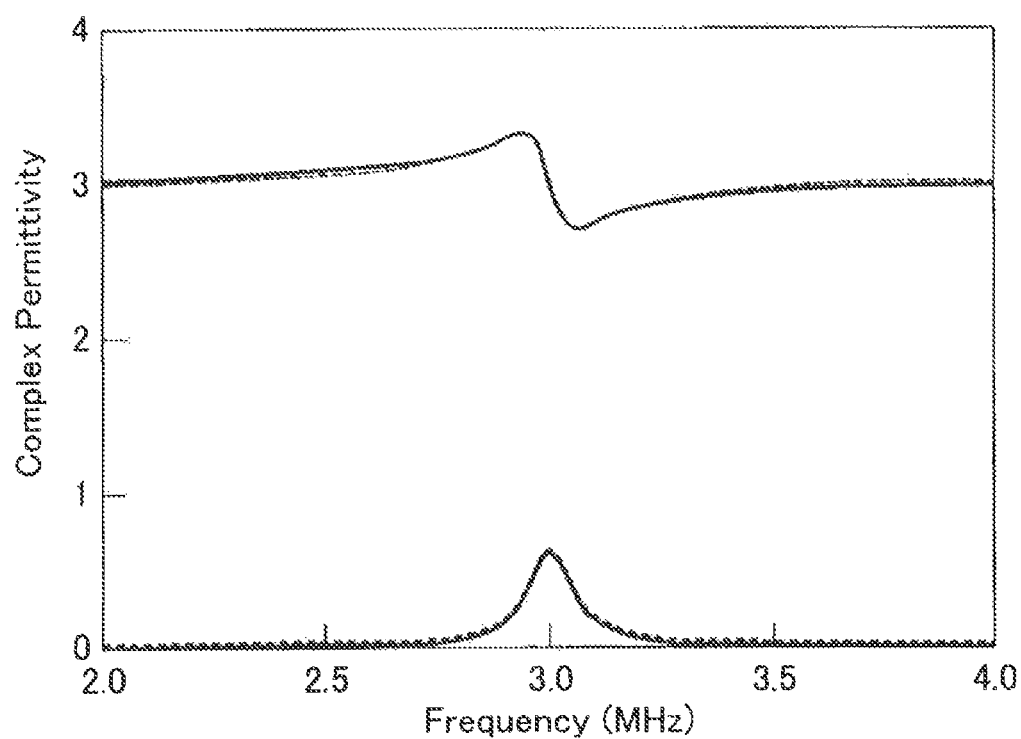
FIG. 3 is a graph showing a frequency characteristic of the complex dielectric constant of the 3rd resonance component in the piezoelectric material of FIG. 2 and the piezoelectric material which has the primary resonance mode of thickness resonance at 3 MHz.
Figure 4:
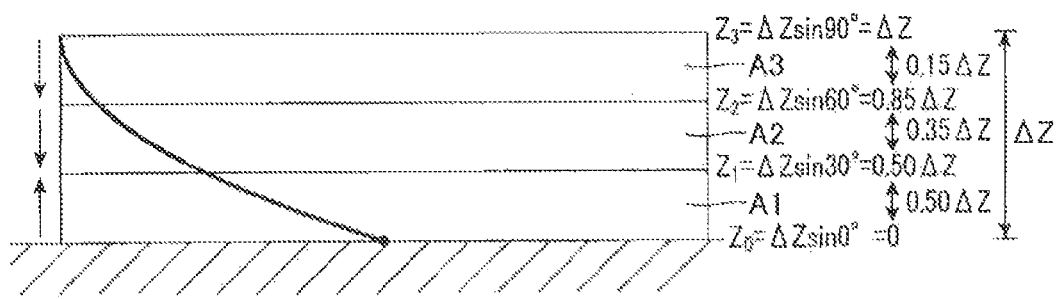
FIG. 4 is a schematic sectional drawing of λ/4 resonance state in a 3-layer piezoelectric transducer.

As air example to be the easiest to understand, $\lambda/4$ transducer will be described in which three piezoelectric materials A1, A2, and A3 are laminated as shown in FIG. 4. In an excitation state of the $\lambda/4$ transducer at $\lambda/4$, the above-mentioned three piezoelectric materials A1, A2, and A3 expand and contract in synchronization, and maximum expansion and contraction shall be $\Delta Z$ on the whole. Provided that the coordinate of the back surface of the piezoelectric material A1 of the 1st layer which touches a fixed end, i.e., the de-matching layer which has sufficiently larger acoustic impedance than that of a piezoelectric material, is set to $z_0$, a displacement of the position accompanying the above-mentioned expansion and contraction is $z_0 = \Delta Z \sin 0° = 0$. On the other hand, a displacement of the coordinate $z_1$ of the surface of the piezoelectric material A1 of the 1st layer is $z_1=\Delta Z \sin 30°=0.5\Delta Z$, a displacement of the coordinate $z_2$ of the surface of the piezoelectric material A2 of the 2nd layer is $z_2=\Delta Z \sin 60°=0.85\Delta Z$, and a displacement of the coordinate $z_3$ of the surface of the 3rd layer of the piezoelectric material A3 of the 3rd layer which touches a free end, i.e. the space having acoustic impedance larger than 0 but sufficiently small is $z_3=\Delta Z \sin 90°=1.0\Delta Z$. Herein, front and back surface of the piezoelectric material A1, A2, and A3 are decided as follows: when the piezoelectric material is pressurized in the thickness direction, a surface where generates voltage of + is defined as the front surface and a surface where generates voltage of − is defined as the back surface.

Namely, in the case of the three layer piezoelectric materials A1, A2 and A3 of FIG. 4, among the whole expansion and contraction $\Delta Z$, the piezoelectric material A1 at the side of a fixed end covers expansion and contraction of $0.5\Delta Z$, the piezoelectric material A2 of the 2nd layer covers expansion and contraction of $0.35\Delta Z$, and the piezoelectric material A3 of the 3rd layer covers expansion and contraction of only $0.15\Delta Z$. Thus, by $\lambda/4$ resonance of a fundamental wave in the laminated piezoelectric material, each piezoelectric material A1, A2, and A3 expands and contracts synchronously (in the same direction), but do not expand and contract uniformly and have uneven strain distribution.

Figure 5:
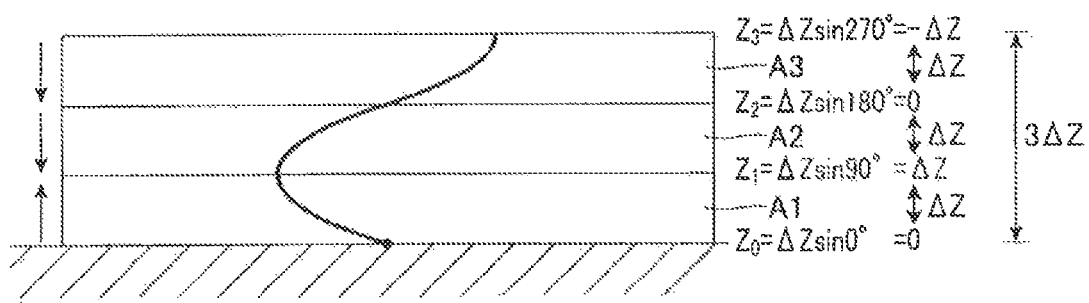
FIG. 5 is a schematic sectional drawing of 3λ/4 resonance state to a 3-layer piezoelectric transducer of FIG. 4.

On the other hand, when the same laminated piezoelectric material is resonated in $3\lambda/4$ resonance, result is shown in FIG. 5. That is, the coordinate $z_0$ of the back of the piezoelectric material A1 of the 1st layer is $z_0=\Delta Z \sin 0°=0$. Displacement of the coordinate $z_1$ of the surface of the piezoelectric material A1 of the 1st layer is $z_1=\Delta Z \sin 90°=\Delta Z$. Displacement of the coordinate $z_2$ of the surface of the piezoelectric material A2 of the 2nd layer is $z_2=\Delta Z \sin 180°=0$. Displacement of the coordinate $z_3$ of the surface of the piezoelectric material A3 of the 3rd layer is $z_3=\Delta Z \sin 270°=-\Delta Z$. Therefore, the piezoelectric material A1 of the 1st layer performs expansion of $\Delta Z$, and the piezoelectric material A2 of the 2nd layer and the 3rd layer and A3 perform contraction of $\Delta Z$.

Thus, an inventor of the present invention focuses attention on such uneven strain distribution. With respect to the piezoelectric material at a mismatched part (corresponding to the sign of "−"), the front and back surface of the piezoelectric material is reversed and laminated so that the remanent polarization (ferroelectrics such as PZT or PVDF) or C axis or A axis of crystals (such as rock crystal) (axis which determines the sign of $d_{33}$, $e_{33}$, $d_{11}$, and $e_{11}$) of each piezoelectric material may coincide with the direction of the sign of the electric displacement or electric field in the strain distribution at the time of transmission and reception of higher resonance component. In the case of FIGS. 4 and 5, as shown by the arrow of the left-hand side, the piezoelectric material A2 and A3 each of the 2nd layer and the 3rd layer are laminated so that the above-mentioned direction of the remanent polarization or crystal axis is opposite to the direction of the piezoelectric material A1 of the 1st layer. Thereby, the primary resonance component is canceled as the result of $0.5\Delta Z+0.35(-\Delta Z)+0.15(-\Delta Z)=0$, as well as the component of the 3rd resonance can be extracted as the result of $1\Delta Z+(-1)(-\Delta Z)+(-1)(-\Delta Z)=3\Delta Z$.

On the other hand, the case where the transmission-and-reception of the n-th resonance component in $\lambda/4$ transducer laminated by n layer piezoelectric materials (n is an integer of 4 or more) will be described with reference to FIG. 6. In order to simplify a model, one end of the laminated layer is fixed to the de-matching layer, and another end is free end. The influences of an acoustic matching layer, a back (backing) layer, and the influence according to the thickness of an adhesion layer shall be excluded.

Figure 6:
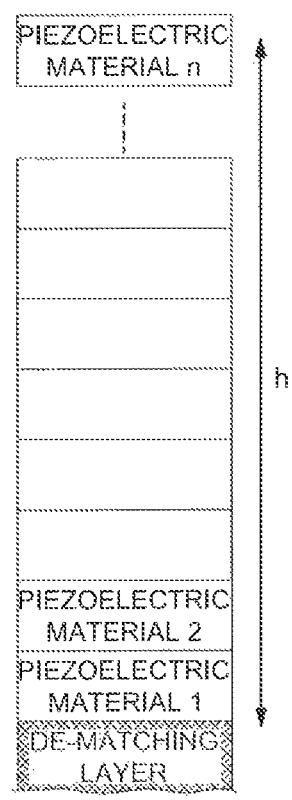
FIG. 6 is a schematic sectional drawing of a n-layer piezoelectric transducer.

7a, 7b and 7c are schematic figures showing a displacement and a strain at the time of the n-layer piezoelectric transducer of FIG. 6 in case of exciting or detecting the n-th resonance component. FIG. 7a shows a laminated state, FIG. 7b shows a displacement of each layer at one moment and FIG. 7c shows a polarity of strain. Similar to above-mentioned FIG. 4 or 5, the interface of a de-matching layer and the piezoelectric material touched thereto shall be the origin $z_0$, and the coordinates of the height (thickness) direction of an element shall be $z_1, z_2, z_3, \ldots, z_n$. In a laminated piezoelectric material, displacement of each piezoelectric material forms a sine wave having the origin $z_0$ at the boundary of a de-matching layer and the piezoelectric material 1 of the 1st layer.

Generally, when a n-th resonance component ($n \geq 1$) is excited in the thickness direction, a displacement $\xi(z)$ at height z is known to be as follows (Kiso Butsurigaku Sensho 8: Shindou and Wave motion written by Masataka Ariyama, Shokabo Publishing):

$$\xi(z,t)=\xi_0 \sin(n\pi/2 \cdot z/h)(\cos n\omega_r t+\theta) \quad (11)$$

Herein, $\omega_r$ is a resonance frequency $2\pi f_r$ of a laminated piezoelectric material, $\theta$ is a phase difference between a stress and a displacement at the time of receiving voltage or a sound wave. Coefficient $\xi_0 \sin(n\pi/2 \cdot z/h)$ means an amplitude of a displacement at height z. Hereafter, a time clause will be omitted.

In this case, the displacement $\xi(z_1)$ at the coordinate $z_1$ is:

$$\xi(z_1)=\xi_0 \sin(n\pi/2 \cdot z/h) \quad (12).$$

Herein, since the displacement $\xi(z)$ has a relationship with a strain S:

$$dS=d\xi/dz \quad (13),$$

the strain $S_m$ of the piezoelectric material of the m-th layer will be represented by $$S_m=[\xi(z_m)-\xi(z_{m-1})]/(z_m-z_{m-1}) \quad (14),$$

wherein m=1 to n and $z_0=0$.

Therefore, strain $S_1$ of the piezoelectric material 1 is $$S_1=\Delta h_1/h_1=\xi_0 \sin(n\pi/2 \cdot h_1/h)/h_1 \quad (15).$$

Herein, $\Delta h_1$ is a thickness change of the piezoelectric material 1, and $\xi(z_1)-\xi(z_0)$ and $h_1$ is a thickness of the piezoelectric material 1. With respect to the piezoelectric material 2, strain $S_2$ is similarly $$S_2 = \Delta h_2/h_2 \quad (16)$$
$$= \xi_0\{\sin(n\pi/2 \cdot (h_1+h_2)/h) - \sin(n\pi/2 \ldots h_1/h)\}/h_2.$$

Strain $S_m$ of the piezoelectric material of the m-th layer is $$S_m = \Delta h_m/h_m \quad (17)$$
$$= \xi_0\{\sin(n\pi/2 \ldots z_m/h) - \sin(n\pi/2 \ldots z_{m-1}/h)\}/h_m.$$

The above-mentioned Expression (17) means that strain of the piezoelectric material in the m-th layer is determined by $\sin(np/2 \cdot n_m/h) - \sin(np/2 \cdot z_{m-1}/h)$, and does not expand and contract uniformly as mentioned above. Therefore, it is understood feat by reversing the front and back surface of a piezoelectric material in the piezoelectric material having positive sign and negative sign, whereby the direction of the electric displacement by the direct piezoelectric effect or an electric field can be coincided with the remanent polarization, and the electrical signal of the n-th resonance component of a piezoelectric element can be efficiently acquired.

Further, when thickness of each piezoelectric material is equal, it can be simplified to:

$$Z_m=(m/n)h, \ z_{m-1}=(m-1/n)h, \ h_m=h/m \quad (18).$$

By substituting this into Expression (17), $$S_m=m\xi_0\{\sin(m\pi/2)-\sin[(m-1)\pi/2]\}/h \quad (19).$$

Next, an electric system will be considered. Electric displacement (charge per unit area of the electrode surface) Dm of the piezoelectric material of the m-th layer produced by the direct piezoelectric effect is:

$$D_m=e_{33}S_m \text{ or } D_m=d_{33}S_m=d_{33}sT_m \quad (20).$$

Herein, s is the elastic compliance of a piezoelectric material. When each piezoelectric materials are connected in electrically parallel, the net electric displacement $D_{Total}$ as an output of a laminated piezoelectric material is:

$$D_{Total} = \sum_{m=1}^{n} D_m \quad (21)$$

Therefore, when the electric capacitance of each piezoelectric material is C, the capacity of a laminated piezoelectric material, will be nC and the electrical impedance decreases to 1/n of one layer piezoelectric material.

Figure 8:
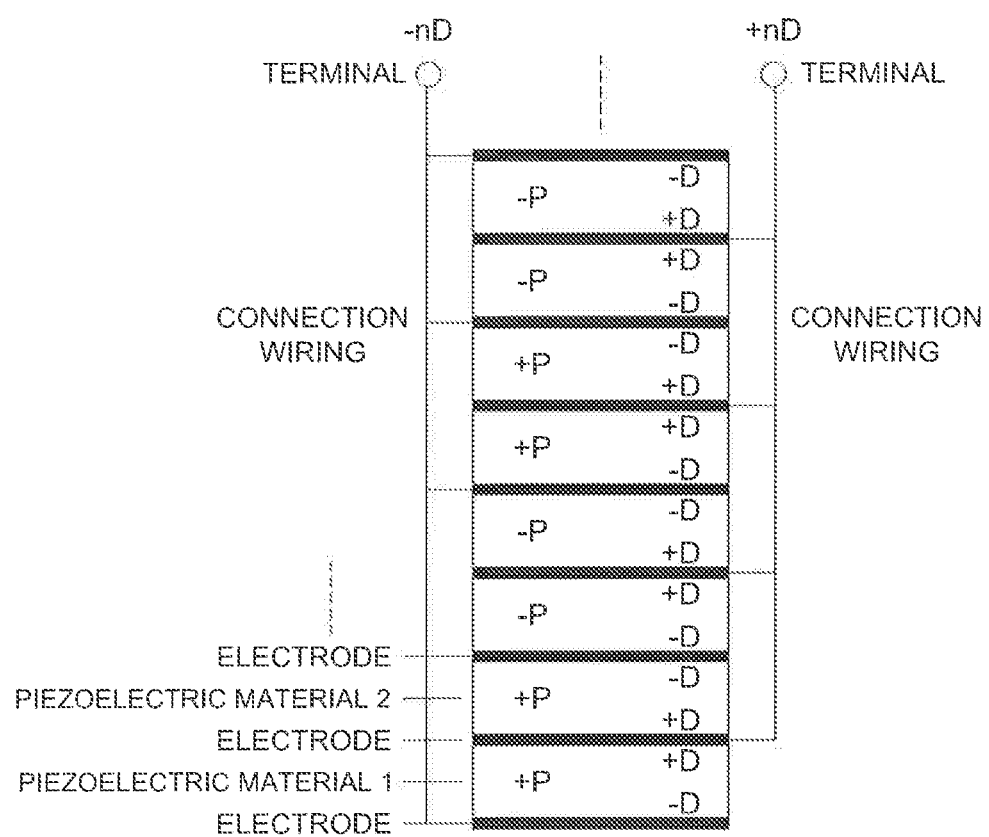
FIG. 8 is a figure showing the relationship between direction of the remanent polarization of each piezoelectric material and the electric displacement by the direct piezoelectric effect at the time of detecting the n-th resonance component in a n-layer piezoelectric transducer of 7a, 7b and 7c.

The inventor of the present invention found out the regularity of the arrangement of the remanent polarization and the C or A axis of crystal thorn the above-mentioned Expression (19) and (21) in which a simple parallel connection can be realized and the laminated piezoelectric material can output the maximum net electric displacement. Moreover, the inventor of the present invention found out followings. When number n (n is 3 or more) of a laminated material layers coincides with an order of harmonics, a node and air anti-node of an elastic wave propagated in the piezoelectric material can be coincided with the boundary of piezoelectric materials, whereby the phase of the strain of each piezoelectric material is reversed 180° without changing an absolute value. For example, when each piezoelectric material is connected in series as shown, in 7a, 7b and 7c and the strain of the piezoelectric material 1 is +, then the periodicity of "+, −, −, +" can be found in every four layers, whereby the n-th resonance component can be detected more efficiently. Theoretical explanation thereof is as follows:

An example of a relationship between direction of the remanent polarization of each piezoelectric material and the electric-displacement D (C/m²) by the direct piezoelectric effect at the time of detecting the n-th resonance component in a n layer piezoelectric material of the present invention will be shown in FIG. 8. The electrodes are provided between the piezoelectric material layers and on both end surfaces of the laminated piezoelectric material, and the two electrodes each located at outermost side of adjacent piezoelectric material pair are connected by connection wiring, resulting in each piezoelectric materials being in an electrically parallel connection. Further, the remanent polarization is orientated to z axis. In the figures, the direction of the remanent polarization of the piezoelectric material 1 is represented by +P for convenience. This direction is shown only for the purpose of distinguishing whether the remanent polarization of other piezoelectric material has the same or opposite direction from to that of the piezoelectric material 1 and does not restrict the polarization direction of the piezoelectric material 1.

As shown in the above-mentioned FIG. 7c, there is periodicity in strain of each piezoelectric material (in the case of FIG. 7c, each piezoelectric material is in-series connection as mentioned above). Therefore, when direction of remanent polarization is made parallel, in order to attain the high charge output or high electric potential output which is the purpose of the present invention, since each electrode has to be insulated electrically and independently wired, whereby it has high risk of a structure and a manufacturing.

In the present invention, in the case of the parallel connection shown in FIG. 8, the remanent polarization of the piezoelectric material has the periodicity of "+P, +P, −P, −P" in every four layers. Namely, the axis of the 1st layer piezoelectric material adjacent to a de-matching layer is used as the basic relationship, the 2nd layer piezoelectric material adjacent to the 1st layer piezoelectric material is set to have the same direction as the basic relationship, further the 3rd and 4th layer piezoelectric materials thereon are set to have the opposite directions, and thereafter, for every four-layer set of piezoelectric materials, the direction is arranged so that it may have the periodicity of "the same direction, the same direction, an opposite direction, and an opposite direction" based on the basic relationship. In another word, the relationship between the direction of an electric displacement or an electric field by the direct piezoelectric effect and a direction of remanent polarization is arranged so that it may have the following periodicity: the relationship between the direction of an electric displacement or an electric field by the direct piezoelectric effect and a direction of remanent polarization of the 1st layer piezoelectric material is used as the basic relationship, the 2nd layer piezoelectric material adjacent to the 1st layer piezoelectric material and the 3rd piezoelectric material each is arranged to have an opposite relationship to the base, and 4th layer piezoelectric materials thereon is arranged to have the same relationship, and thereafter, for every four layers set of piezoelectric materials, the relationship is arranged so that it may have the periodicity of "the same relationship, an opposite relationship, an opposite relationship, and the same relationship". According to this arrangement, not only the electrical impedance can be lowered by 1/n of the piezoelectric material of one layer, but the charge sensitivity between both terminals can be amplified n-fold easily.

Herein, the direction of the piezoelectric material is not limited to be the same in every four layers as described above, however the direction of the 1st layer piezoelectric material may be arranged as arbitrary directions with four layers in one unit. In this case, as described above, the relationship between the direction of an electric displacement or an electric field by the direct piezoelectric effect and a direction of remanent polarization of the 1st layer piezoelectric material is used as the basic relationship, the relationship of the 2nd layer piezoelectric material adjacent to the 1st layer piezoelectric material and the 3rd piezoelectric material each may be arranger to have an opposite relationship to the basic relationship, and 4th layer piezoelectric materials thereon may be arranger to have the same relationship. Namely, the relationship between the direction of an electric displacement or an electric field by the direct piezoelectric effect and a direction of remanent polarization of the (4P+1)th layer piezoelectric material (P is 0 or a positive integer) is used as the basic relationship, the relationship of the (4P+2)th layer piezoelectric material adjacent thereto and the (4P+3)th piezoelectric material each may be arranger to have an opposite relationship to the basic relationship, and (4P+4)th layer piezoelectric materials thereon may be arranger to have the same relationship. Herein, the whole numbers of the laminated piezoelectric material layers are not limited to a multiple number of the above described periodicity.

Further, at the time of transmission of an ultrasound, the voltage on which an alternating current component is superimposed to a direct-current component may be applied to the piezoelectric material. In such a case, only the sign of the electric field by the alternating current component in the applied voltage may be taken into consideration as a sign of an electric field.

Above mentioned case is an example where the n-th resonance component is detected. Conversely, in the case of transmitting a n-th resonance component, it improves an efficiency than conventionally connecting an oscillator between terminals in FIG. 8. In the case of transmission, a relationship between strain S and applied electric held E is:

$$S=dE \text{ or } S=(e/c)E \tag{22}$$

A voltage generator is connected between the both terminals of the laminated piezoelectric material shown in FIG. 8, and the voltage is applied in a frequency corresponding to the n-th resonance component, thereby a strain shown in FIG. 8 and a displacement shown in FIG. 7b can be produced, and an ultrasound wave can be excited into a medium. From the previously described relationship of the electrical impedance, a low-voltage high electric current drive is performed in the case of the structure of the present invention.

FIGS. 9a, 9b, 9c and 9d are schematic figures showing the structure of 2n-layer piezoelectric transducer for detecting the n-th resonance component FIG. 9a shows a laminated state, FIG. 9b snows a displacement of each layer at one moment and FIG. 9c and FIG. 9d respectively shows a coefficient of a strain and an electric displacement. The above-mentioned coefficient of 0.3 and 0.7 represents a relative ratio of each strain and electric displacement and does not represent an absolute value. Herein, it approximated with $\frac{1}{2}^{1/2} \approx 0.7$. Electrode is provided between the piezoelectric material layers and on both end surfaces of the laminated piezoelectric material and a plurality of the piezoelectric materials are in an electrically parallel connection each other mutually by connecting two electrodes each located at outermost side of adjacent piezoelectric material pair. In this case, the electric displacement by the direct piezoelectric effect is the same, but a capacitance becomes twice and electrical impedance is halved comparing with the previously described n-layer piezoelectric transducer. The remanent polarization is arranged in a repetitive manner as "+P, −P, −P, +P, −P, +P, +P, −P" in every eight layers based on the piezoelectric material touched to a de-matching layer.

Strain $Sm^{n\omega}$ of each piezoelectric material is given by Expression (23).

$$Sm^{n\omega}=2n\xi_0^{n\omega}\{\sin [m(\pi/4)]-\sin [(m\cdot 1)(\pi/4)]\}/h, m=1, 2,\ldots,2n \tag{23}$$

EXAMPLES

Example 1

Examples according to an above-mentioned view will be detailed below. At first, detection of 3λ/4 resonance component by 2-layer piezoelectric transducer shown in FIG. 10 will be described as the 1st example. A 2-layer piezoelectric transducer has the simplest structure in a laminated piezoelectric material. In this case, the order of the resonance component is not in agreement with the lamination number used for a transmission-and-rejection. However, the efficiency of a transmission-and-reception can be raised by applying the present invention as follows.

The strains $S_1$ and $S_2$ of the piezoelectric materials 1 and 2 of FIG. 10 each is:

$$S_1=\Delta h_1/h_1=\xi_0 \sin(n\pi/2-h_1/h)/h_1 \tag{24}$$

$$S_2=\Delta h_2/h_2=\xi 0\{\sin(n\pi/2)-\sin(n\omega/2-h_1/h)\}/h_2 \tag{25}$$

Herein, h represents a height of a laminated piezoelectric material, $h_1$ and $h_2$ each represents a height of each piezoelectric material, and $h_1=h_2=h/2$.

The response to 3λ/4 resonance component is given by n=3. In that case, strain $S_1^{3\omega}$ and $S_2^{3\omega}$ each is:

$$S_1^{3\omega} = 2\xi_0^{3\omega}\sin(3\pi/4)/h = 2(\xi_0^{3\omega}/2^{1/2})/h \tag{26}$$

$$S_2^{3\omega} = 2\xi_0^{3\omega}\{\sin(3\pi/2) - \sin(3\pi/4)\}/h \tag{27}$$
$$= -2\xi_0^{3\omega}/(1+1/2^{1/2})/h.$$

Subscript 3ω represents a displacement in a 3rd resonance component. Herein, as it approximated with $\frac{1}{2}^{1/2} \approx 0.7$, these expressions show that an amplitude ratio in strains of the piezoelectric material 2 and the piezoelectric material 1 is −1.7:+0.7 in a 3rd resonance component.

Displacement and sign of strain of such each piezoelectric material are shown in FIGS. 11a and 11b. FIG. 11a shows a displacement and FIG. 11b shows a strain. The strain ratio of the piezoelectric material 1 and the piezoelectric material 2 is as shown in FIG. 11b. The absolute values of strains of each piezoelectric material do not coincide with because a boundary of each piezoelectric material does not coincide with a position of node and anti-node of displacement as mentioned above.

When piezoelectric materials are in an electrically parallel connection each other mutually by connecting two electrodes each located at outermost, side of adjacent piezoelectric material pair as shows in FIG. 12, electrical impedance of a laminated piezoelectric material becomes ½ of the impedance of one piezoelectric material. Further, the electric displacement $D_{1,-1}^{3\omega}$ by the direct piezoelectric effect is represented by Expression (28), provided that a direction of the remanent polarization of the piezoelectric material 1 and those of the piezoelectric material 2 is same, thereby the electric displacement is calculated by adding by reversing one of polarity in a parallel connection.

$$D_{1,-1}^{3\omega}=2(1+2^{1/2})e\xi_0^{3\omega}/h \tag{28}$$

On the other hand, response to a primary resonance component can be realized as the case of n=1 in Expressions (24) and (25). Namely, strain $S_1^{\omega}$ and $S_2^{\omega}$ each is:

$$S_1^{\omega}=2\xi_0^{\omega} \sin(\pi/4)/h=2(\xi_0^{\omega}/2^{1/2})/h \tag{29}$$

$$S_2^{\omega}=2\xi_0^{\omega}\{\sin(\pi/2)-\sin(\pi/4)\}/h=2\xi_0\omega\{1-\frac{1}{2}^{1/2}\}/h \tag{30}$$

Herein, when parallel connection as shown in FIG. 12 is performed and direction of remanent polarization is set to the same direction, the electric displacement $D_{1,1}^{\omega}$ is:

$$D_{1,1}^{\omega}=2e\xi_0^{\omega}(2^{1/2}-1)/h \tag{31}$$

Herein, subscript 1 corresponds to a direction of the remanent polarization of each piezoelectric material, and shows a direction of the remanent polarization of the piezoelectric material 1 and the piezoelectric material 2 from the left.

The above result shows that sensitivity can be amplified 2.4 times for $3\lambda/4$ resonance component and sensitivity can be simultaneously dropped to 0.4 time for $\lambda/4$ resonance component, by taking in consideration of strain of each piezoelectric material, and arranging a direction of remanent polarization being the same in the case of a parallel connection. Therefore, when the present invention is applied to the ultrasound transducer which consists of a 2-layer piezoelectric material, it will be possible to transmit and receive the signal by $3\lambda/4$ resonance by a high S/N ratio.

Figure 13A:
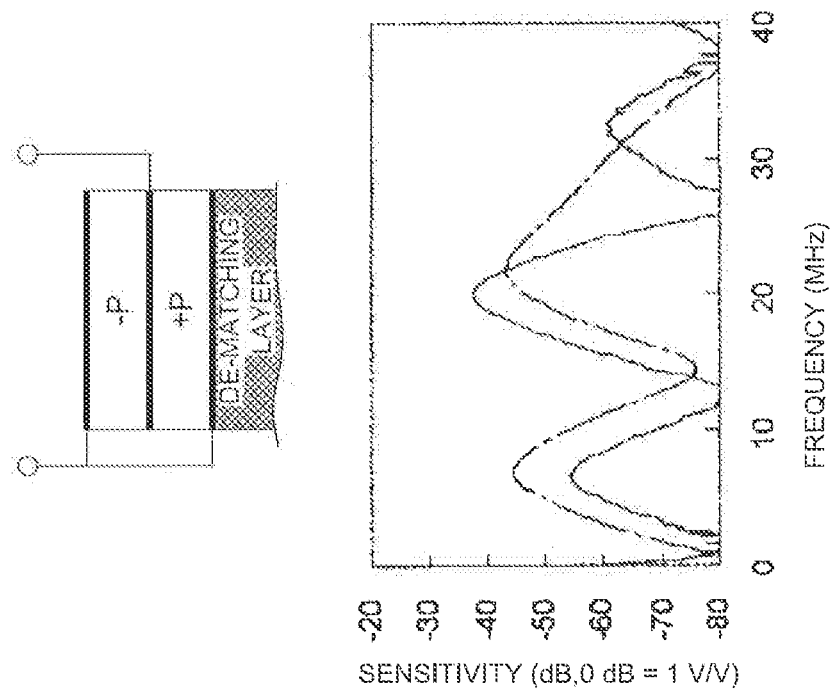
FIGS. 13a and 13b are graphs showing experimental data and a simulation result about the transmission-and-reception characteristics of the ultrasound by the 2-layer piezoelectric transducer of FIG. 10 and its comparative example.
Figure 13B:
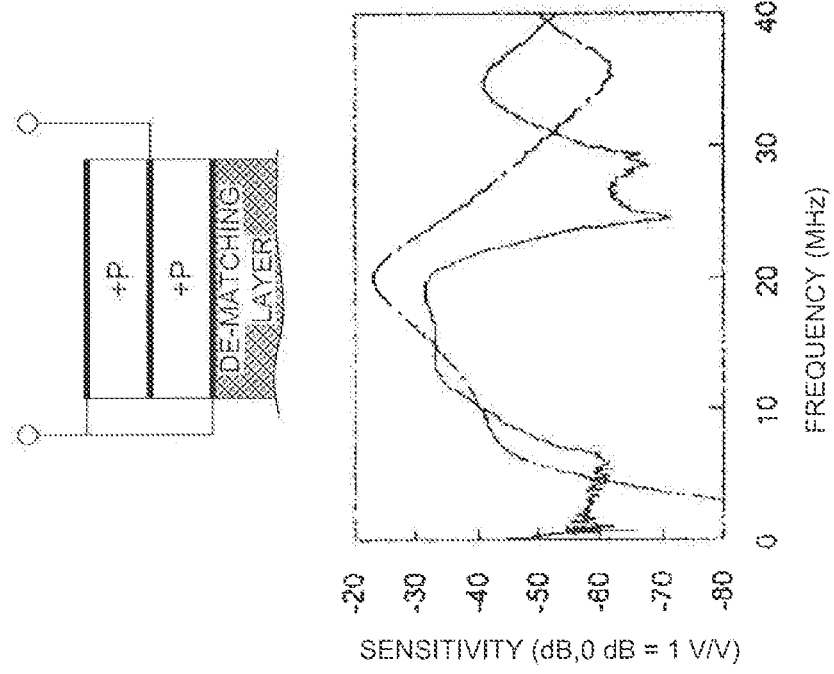

FIGS. 13a and 13b are graphs showing experimental data and a simulation result about the transmission-and-reception characteristics of the ultrasound transducer by the 2-layer piezoelectric material using P(VDF/TrFE) (polyvinylidene fluoride-ethylene trifluoride copolymer). A solid line shows an experimental result and a chain line shows a simulation result. Surfaces of electrodes formed on the outermost side, namely outside surface of adjacent piezoelectric material pair are electrically connected in parallel each other mutually. $\lambda/4$ resonance frequency is 7 MHz and $3\lambda/4$ resonance frequency is about 20 MHz. FIG. 13a shows a result when a direction of polarization is set as the same direction based on this invention and FIG. 13b shows a result of an opposite direction as reference. When the direction of polarization and the wiring technique based on the present invention are combined as shown in FIG. 13a, $3\lambda/4$ resonance peaks shown at 20 MHz is larger than $\lambda/4$ resonance peaks shown at 7 MHz. $3\lambda/4$ resonance peaks increases 20 dB as compared with the result shown in FIG. 13b. Thus, by combining a direction of polarization and the wiring technique based on the technique of the present invention in a 2-layer piezoelectric material, the 3rd resonance component can be increased as well as the fundamental component can be attenuated.

Example 2

Figure 14:
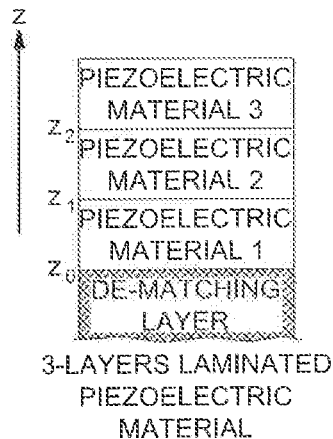
FIG. 14 is a detailed Example according to the view of the present invention shown by FIGS. 8 and 5, and is a schematic sectional drawing showing the structure of a 3-layer piezoelectric transducer.

Subsequently, detection of the 3rd resonance component by a 3-layer piezoelectric transducer will be described. Schematic structural drawing is shown in FIG. 14. This transducer is a $\lambda/4$ transducer which fixes the one end of a laminated piezoelectric material to a de-matching layer, and another end is a free end.

Design process based on the present invention will be described first. Similar to above description, the coordinate of the height (thickness) direction of an element is set to z based on the boundary of a de-matching layer and a piezoelectric material 1 as the origin. Next, strain S occurred on each piezoelectric material will be considered. The piezoelectric material 1, the piezoelectric material 2, and the piezoelectric material 3 are laminated in this order from the base side. Coordinate z is set as Z=0 at the boundary of the base and the piezoelectric material 1, to $z_1$ at the boundary of the piezoelectric material 1 and the piezoelectric material 2, to $z_2$ at the boundary of the piezoelectric material 2 and the piezoelectric material 3, and to $z_3$ at the end of the piezoelectric material 3. Further, a thickness of the piezoelectric material 1 is set to $h_1$, a thickness of the piezoelectric material 2 is set to $h_2$, and a thickness of the piezoelectric material 3 is set to $h_3$, and a height of a laminated piezoelectric material is set to h.

Then, since displacement $\xi(z_1)$ at coordinate z1 is:

$$\xi(z_1)=\xi_0 \sin(n\pi/2 \cdot z_1/h) \tag{32}$$

strain $S_1$ of the piezoelectric material becomes Expression (33).

$$S_1=\Delta h_1/h_1=\xi_0 \sin(n\pi/2 \cdot h_1/h)/h_1 \tag{33}$$

Similarly, strain of the piezoelectric materials 2 and 3 each is set to Expressions (34) and (35).

$$S_2=\Delta h_2/h_2=\xi_0\{\sin(n\pi/2-(h_1+h_2)/h)-\sin(n\pi/2-h_1/h)\}/h_2 \tag{34}$$

$$S_3=\Delta h_3/h_3=\xi_0\{\sin(n\pi/2)-\sin(n\pi/2 \cdot (h_1+h_2)/h)\}/h_3 \tag{35}$$

The strain of each piezoelectric material during $3\lambda/4$ resonance is given by the case of n=3 in above-mentioned Expressions (33) to (35). When the thickness of each piezoelectric material is equal, namely, $h_1=h_2=h_3=h/3$ in the above-mentioned Expressions, strain $S_1^{3\omega}$, $S_2^{3\omega}$ and $S_3^{3\omega}$ of each piezoelectric material is:

$$S_1^{3\omega}=\Delta h_1^{3\omega}/h_1=3\xi_0^{3\omega}\sin(\pi/2)/h=3\xi_0^{3\omega}/h \tag{36}$$

$$S_2^{3\omega}=\Delta h_2^{3\omega}/h_2=3\xi_0^{3\omega}\{\sin(\pi)-\sin(\pi/2)\}/h=-3\xi_0^{3\omega}/h \tag{37}$$

$$S_3^{3\omega}=\Delta h_3^{3\omega}/h_3=3\xi_0^{3\omega}\{\sin(3\pi/2)-\sin(\pi)\}/h=-3\xi_0^{3\omega}/h \tag{38}$$

Herein, subscript $3\omega$ means the response in the 3rd resonance component. These Expressions show that strains of the piezoelectric material 2 and the piezoelectric material 3 are in opposite phases to the strain of the piezoelectric material 1 in the case of $3\lambda/4$ resonance.

Figure 15A:
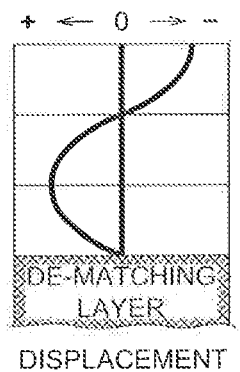
FIGS. 15a and 15b are figures for explaining displacement and a strain at the time of transmission-and-reception of the higher resonance component in the 3-layer piezoelectric transducer of FIG. 14.
Figure 15B:
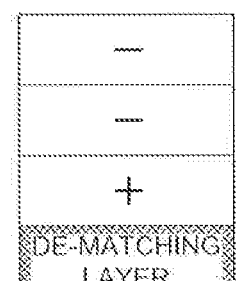

Displacement and sign of strain of each piezoelectric material is shown in FIGS. 15a and 15b. FIG. 15a shows displacement and FIG. 15b shows strain. Since this example is for a transmission and reception of the 3rd resonance component and the piezoelectric material is 3-layer laminated, whereby the node and anti-node of the displacement corresponds with the boundary of each piezoelectric material as shown in above-mentioned FIGS. 15a, 15b and 5. At this time, provided that strain of the piezoelectric material 1 is set to "+", the strain of each piezoelectric materials 2 and 3 can be encoded as "−", as shown in above-mentioned FIGS. 15b and 5.

Figure 16:
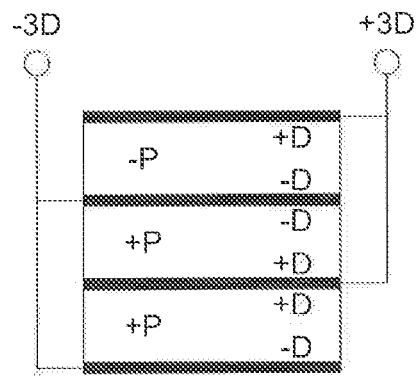
FIG. 16 is a figure showing the relationship between direction of the remanent polarization of each piezoelectric material and the electric displacement by the direct piezoelectric effect at the time of detecting the 3rd resonance component in a 3-layer piezoelectric transducer of FIGS. 14, 15a and 15b.

Based on behavior of the above dynamical system, an optimal structure of an electric system will be drawn. As shown in FIG. 16, electrodes formed on the surface of outermost layer of adjacent piezoelectric material pair are connected and wiring is pulled out and jointed from there, parallel connection of each piezoelectric material can be carried out electrically easily. At this time, the electrical impedance of a laminated piezoelectric material decreases to ⅓ of the 1-layer piezoelectric material. Further, the direction of the remanent polarization, of the piezoelectric material 1 is set as a basis (+P), then the direction of the remanent polarization of the piezoelectric material 2 is set to the same direction (+P) and the direction of the remanent polarization of the piezoelectric material 3 is set to the opposite direction (−P). Namely, the relationship between the direction of an electric displacement or an electric field by the direct piezoelectric effect and a direction of remanent polarization of the 1st layer piezoelectric material is used as the basic relationship, the relationship of the 2nd layer piezoelectric material adjacent thereto and the 3rd piezoelectric material each may be arranger to have an opposite relationship to the basic relationship. Then, the charge induced by wiring will be the total of the charge produced according to the direct piezoelectric effect. The electric displacement $D_{1,1,-1}^{3\omega}$ induced between both terminals at this time is represented by Expression (39).

$$D_{1,1,-1}^{3\omega}=eS_1-e(S_2+S_3)=9e\xi_0^{3\omega}/h \tag{39}$$

Herein, subscripts 1 and −1 correspond to a direction of the remanent polarization of each piezoelectric material, and show a direction of the remanent polarization of the piezoelectric material 1, 2 and 3 from the left.

The response to $\lambda/4$ resonance is given by a case of n=1. The strain $S_1$, $S_2$ and $S_3$ of each piezoelectric material is:

$$S_1 = \Delta h_1/h_1 = 3\xi_0 \sin(\pi/6)/h \tag{40}$$

$$S_2 = \Delta h_2/h_2 = 3\xi_0 \{\sin(\pi/3) - \sin(\pi/6)\}/h \tag{41}$$

$$S_3 = \Delta h_3/h_3 = 3\xi_0 \{\sin(\pi/2) - \sin(\pi/3)\}/h \tag{42},$$

that is $$S_1 = S_2 + S_3 \tag{43}.$$

On the other hand, the electric displacement $D_{1,1,-1}^{\omega}$ according to $\lambda/4$ resonance in the parallel connection shown in FIG. 16 is:

$$D_{1,1,-1}^{\omega} = e(S_1 + S_2 + S_3) = 0 \tag{44}.$$

Above result shows that the sensitivity based on $\lambda/4$ resonance is negated in the example of the present invention comprising 3-layer piezoelectric material.

As comparison, the transmission-and-reception of the 3rd resonance component with the 3-layer piezoelectric material in which remanent realizations are set in parallel will be described. The electric displacement $D_{1,1,1}^{3\omega}$ produced by the direct piezoelectric effect in $3\lambda/4$ resonance in a laminated piezoelectric material is:

$$D_{1,1,1}^{3\omega} = e(S_1 + S_2 + S_3) = -3e\xi_0^{3\omega}/h \tag{45}.$$

Therefore, in the present example, it is understood that die electric displacement between terminals improves 3 times (about 10 dB) in a parallel connection as shown in the above-mentioned Expression (45).

Figure 17:
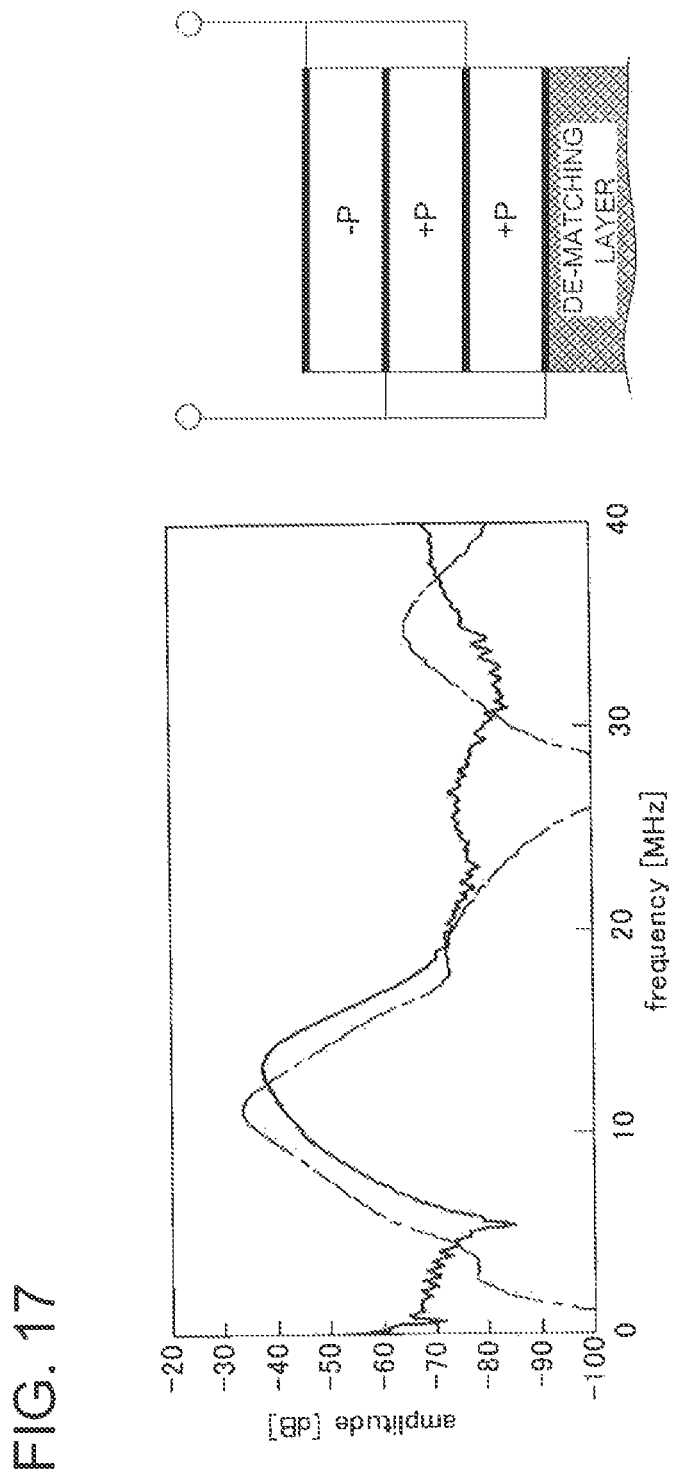
FIG. 17 is a graph showing experimental data and a simulation result about the transmission-and-reception characteristics of the ultrasound by the 3-layer piezoelectric transducer of FIG. 16.

Hereinafter, experimental data and a simulation result about the transmission-and-reception characteristics of the ultrasound by the 3-layer piezoelectric transducer shown, in FIG. 16 are shown in FIG. 17. P(VDF/TrFE) was used in the experiment. Schematic structure of an ultrasound transducer is shown in the right figure of FIG. 17. According to the present invention, the three-layer piezoelectric material is connected in electrically parallel, and the direction of polarization is set as same as shown in FIG. 16. The height of a 3-layer piezoelectric material is about 120 μm and $\lambda/4$ resonance frequency is 4.5 MHz. The solid line in the left figure shows an experimental result, and a chain line shows a simulation result.

From FIG. 17, below 20 MHz, a peak was not found at near 4.5 MHz which corresponds to each resonance frequency, and $\lambda/4$ resonance peaks have disappeared. Therefore, it is understood that the 1st peak in the transducer of the present example is 13.5 MHz which correspond to $3\lambda/4$ resonance.

Figure 18:
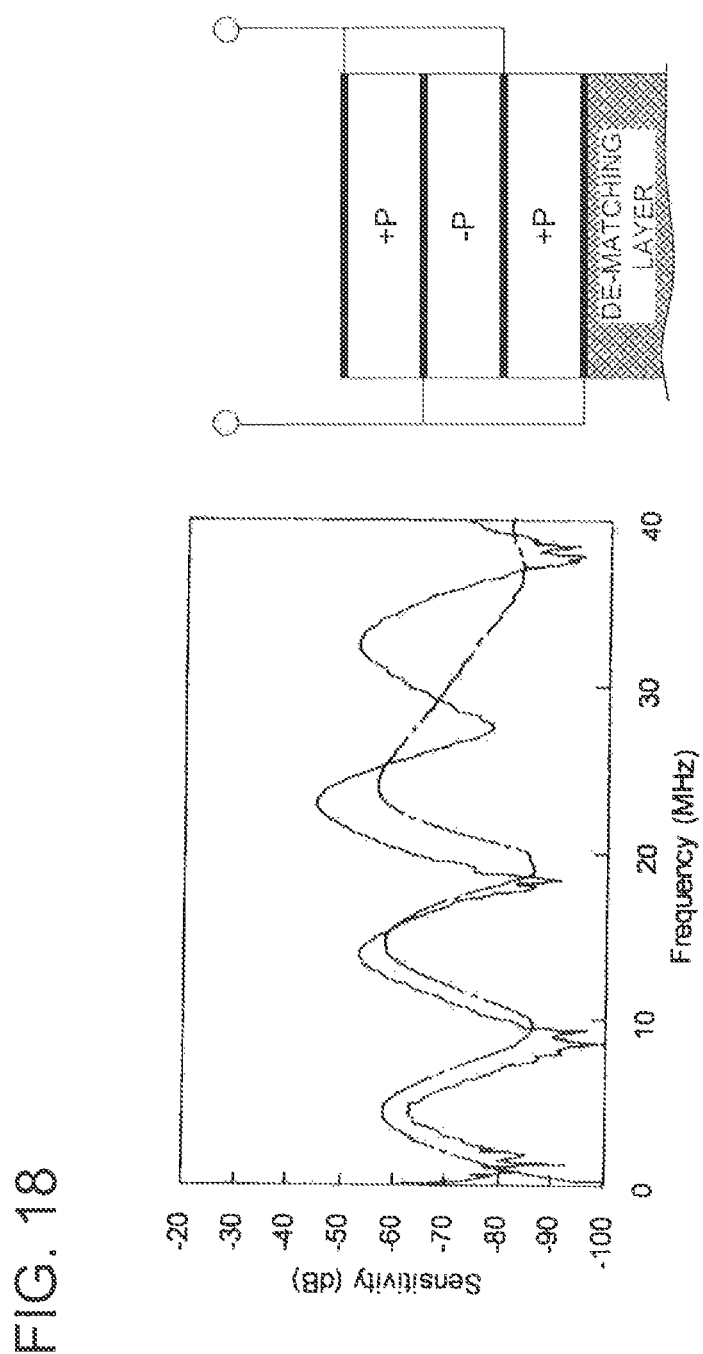
FIG. 18 is a graph showing experimental data and a simulation result about the transmission-and-reception characteristics of the ultrasound by the 3-layer piezoelectric transducer of its comparative example of FIG. 16.

As a comparative example, the characteristics of a laminated piezoelectric material in which direction of the remanent polarization of the piezoelectric materials 2 and 3 are reversed to that in FIG. 17 will be shown in FIG. 18. As shown in the left figure, this 3-layer piezoelectric transducer shows the peak both at 4.5 MHz for $\lambda/4$ resonance and 13.5 MHz for the 3rd resonance component thereof. Further, the sensitivity of the 3rd resonance component is about -50--60 dB which is about 10-20 dB smaller compared to the result of the example shown in FIG. 17. Thus, it is understood that by devising a direction of polarization based on the technique of the present invention, the 3rd resonance component can be increased as well as the fundamental wave component can be attenuated.

In the 2nd example, the technique of the transmission-and-reception of the 3rd resonance component by using a 3-layer piezoelectric transducer was described. In this technique, the order of the resonance component of the laminated piezoelectric material coincides with the number of laminated layers, whereby (i) the vibration mode of each piezoelectric material can be understood by coding by coinciding the interface of piezoelectric materials with the node and anti-node of an elastic wave of a piezoelectric material, and based on the sign and wiring technique, (ii) by arranging suitably direction of the remanent polarization of each piezoelectric material in the same direction or an opposite direction, the sensitivity at transmission and reception can be amplified 3 times (about 10 dB) for $3\lambda/4$ resonance component and simultaneously $\lambda/4$ resonance component can be canceled such as the function of filter, compared with the case where the direction of the remanent polarization of each piezoelectric material is simply set to the same direction. Moreover, by connecting in electrically parallel connection, electrical impedance can be decreased to ⅓. As mentioned above, this invention is largely effective in the case of the transmission-and-reception of the $3\lambda/4$ wave selectively by a high S/N ratio. In the case of reception, it is possible to reduce a band separation filter or amplifier. Or whether it does not result in reduction, order can be reduced to suppress a loss in the case of a filter, and a gain can be small in the case of amplifier.

Example 3

The 3rd example is related to a transmission and reception of the 3rd resonance component by the transducer laminated with 6 layers of piezoelectric materials having the same thickness. This example corresponds to the case in which each piezoelectric material of 3-layer piezoelectric transducer shown in the 2nd example is further divided into two piezoelectric materials. In the case of parallel connection, since electrical impedance not only becomes half further, but an electrode at upper end surface and an electrode at lower end surface are connected, whereby the whole laminated piezoelectric material can be shielded electrically.

Figure 19A:
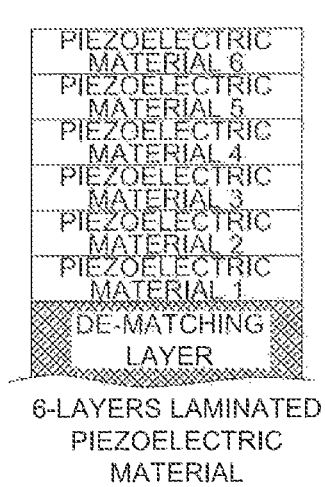
FIGS. 19a, 19b and 19c are other detailed examples according to the view of this invention shown by FIG. 8, and is a schematic sectional drawing showing the structure of a 6-layer piezoelectric transducer.
Figure 19B:
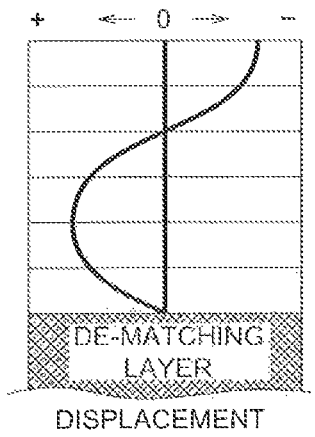
Figure 19C:
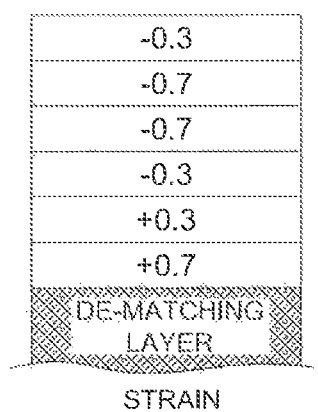

FIG. 19 is sectional drawing in which showing the structure of the 6-layer piezoelectric transducer, and schematically showing a displacement and a strain at the time of the transmission-and-reception of the 3rd resonance component. FIG. 19a shows a lamination status. FIG. 19b shows a displacement of each layer at a certain moment and FIG. 19c shows a coefficient of strain.

The strain $S_1$, $S_2$, $S_3$, $S_4$, $S_5$ and $S_6$ of each piezoelectric material is:

$$S_1 = 6\xi_0 \sin(\pi/4)/h = 6\xi_0(½^{1/2})/h \tag{46}$$

$$S_2 = 6\xi_0 \{(\sin(\pi/2) - \sin(\pi/4)\}/h = 6\xi_0(1 - ½^{1/2})/h \tag{47}$$

$$S_3 = 6\xi_0 \{\sin(3\pi/4) - \sin(\pi/2)\}/h = 6\xi_0(½^{1/2} - 1)/h \tag{48}$$

$$S_4 = 6\xi_0 \{\sin(\pi) - \sin(3\pi/4)\}/h = 6\xi_0(-½^{1/2})/h \tag{49}$$

$$S_5 = 6\xi_0 \{\sin(5\pi/4) - \sin(\pi)\}/h = 6\xi_0(-½^{1/2})/h \tag{50}$$

$$S_6 = 6\xi_0 \{\sin(3\pi/2) - \sin(5\pi/4)\}/h = 6\xi_0(½^{1/2} - 1)/h \tag{51}.$$

Figure 20:
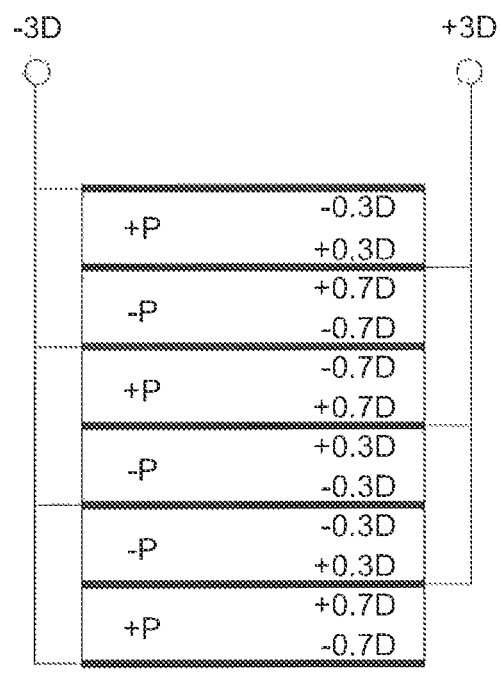
FIG. 20 is a figure showing the relationship between direction of the remanent polarization of each piezoelectric material and the electric displacement by the direct piezoelectric effect at the time of detecting the 3rd resonance component in a 6-layer piezoelectric transducer of FIG. 19.

Herein, as it approximated with $½^{1/2} \approx 0.7$, the ratio of strain in each piezoelectric material become as it is shown in a schematic diagram of FIG. 20.

In the case where two electrodes each located at outermost side of adjacent piezoelectric material pair are connected in an electrically parallel connection, the desirable arrangement of the remanent polarization is shown in FIG. 20. Namely, the relationship between the direction of an electric displacement or an electric field by the direct piezoelectric effect and a direction of remanent polarization of the 1st layer piezoelectric material is used as the basic relationship, the 2nd layer piezoelectric material adjacent to the 1st layer piezoelectric material is arranger to have the same relationship as the basic relationship, and the 3rd to 6th layer piezoelectric material each is arranged to have the opposite relationship. In another word, the relationship between the direction of an electric displacement or an electric field by the direct piezoelectric effect and a direction of remanent polarization is arranged so that it may have the following periodicity: the relationship of the (8P+1)th layer piezoelectric material (P is 0 or a positive integer) adjacent to the de-matching layer is used as the basic relationship, the relationship of the (8P+2)th layer piezoelectric material adjacent thereto is arranged to have the same relationship as the basic relationship, and the (8P+3)th, (8P+4)th, (8P+5)th, and (8P+6)th piezoelectric material each may be arranged to have an opposite relationship to the basic relationship, and (8P+7)th and (8P+8)th layer piezoelectric materials thereon may be arranger to have the same relationship. According to this arrangement, even though a total charge amount is not different from the case of 3-layer piezoelectric material, but the electrical impedance can be lowered by ½ of those.

Figure 21:
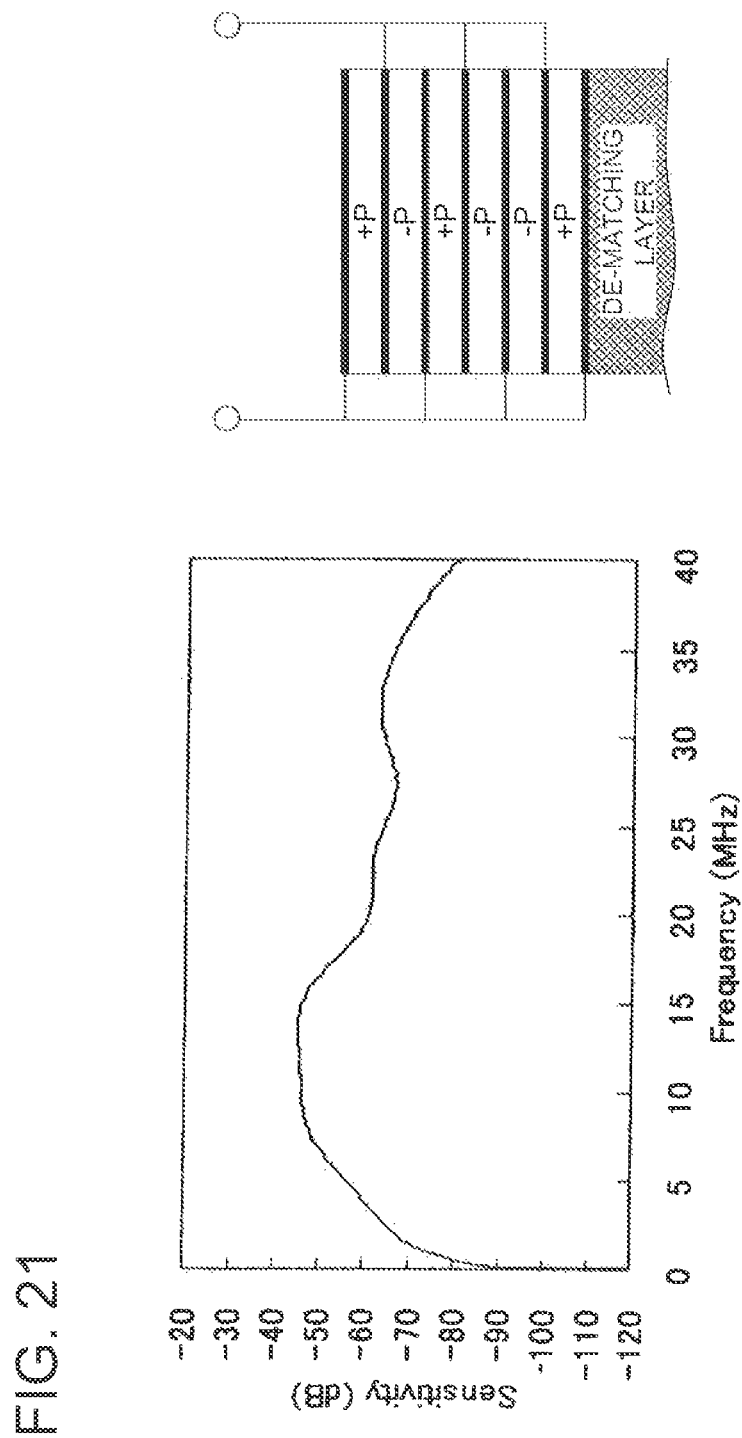
FIG. 21 is a graph showing experimental data and a simulation result about the transmission-and-reception characteristics of the ultrasound by the 6-layer piezoelectric transducer of FIG. 20.

FIG. 21 shows the result of simulation about the frequency characteristics of sensitivity of the in the 6-layer piezoelectric transducer which combined polarization arrangement and wiring as shown in FIG. 20. $\lambda/4$ resonance frequency of this 6-layer piezoelectric transducer is 5 MHz. However, by combining the polarization arrangement and wiring according to the present invention as shown in the right figure, the sensitivity by $\lambda/4$ resonance is decreased, and the sensitivity by $3\lambda/4$ resonance is raised to the maximum as shown in the left figure.

Example 4

Figure 22:
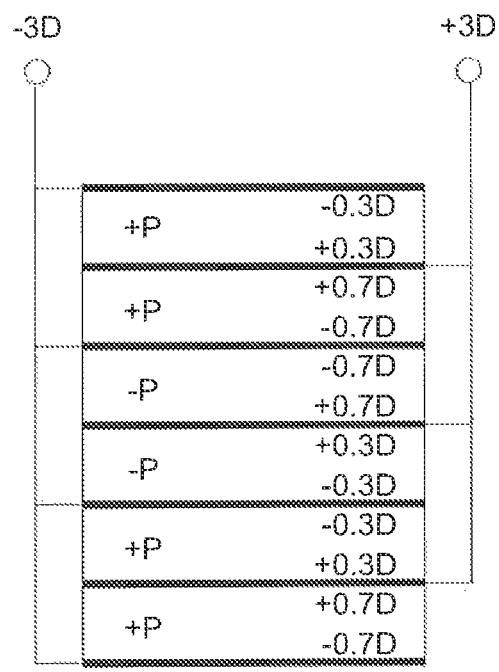
FIG. 22 is a figure showing the relationship between direction of the remanent polarization of each piezoelectric material and the electric displacement by the direct piezoelectric effect at the rime of detecting the 3rd resonance component in a 6-layer piezoelectric transducer of FIG. 19.

The 4th example is a case of transmission and reception of the 3rd resonance component by the transducer which laminated 6 layers of piezoelectric materials having the same thickness. Although this example is the same as the example of the 6-layer piezoelectric transducer shown in the 3rd example, it is different in the arrangement of the remanent polarization in the case of the electric parallel connection as shown in FIG. 22. Namely, the relationship between the direction of an electric displacement or an electric field by the direct piezoelectric effect and a direction of remanent polarization of the 1st layer piezoelectric material is used as the basic relationship, the 2nd and 3rd layer piezoelectric material adjacent thereto is arranger to have an opposite relationship to the basic relationship, the 4th and 5th layer piezoelectric material each is arranged to have the same relationship, and the 6th layer piezoelectric material thereon is arranger to have an opposite relationship to the basic relationship. In another word, the relationship between the direction of an electric displacement or an electric held by the direct piezoelectric effect and a direction of remanent polarization is arranged so that it may have the following periodicity: the relationship of the (4P+1)th layer piezoelectric material (P is 0 or a positive integer) adjacent to the de-matching layer is used as the basic relationship, the (4P+2)th and (4P+3)th layer piezoelectric material adjacent thereto are arranged to have a opposite relationship to the basic relationship, and the (4P+4)th piezoelectric material thereon is arranged to have the same relationship as the basic relationship. Further in other word, the direction of the axis of the 1st layer piezoelectric material is used as the basic relationship, the 2nd layer piezoelectric material adjacent thereto is arranger to have the same direction as the basic relationship, and 3rd and 4th layer piezoelectric material are arranged to have an opposite relationship, and thereafter, for every four-layer-set of piezoelectric materials, the direction, is arranged so that it may have the periodicity of "the same direction, the same direction, an opposite direction, and an opposite direction". According to this arrangement, it results that the sensitivity by $\lambda/4$ resonance is decreased more and the sensitivity by $3\lambda/4$ resonance is amplified more.

In addition, about a direction of the remanent polarization of the piezoelectric material shown in the 4th example, it is not limited to 6-layer laminated transducer, but it may be applicable for any numbers of lamination so long as a transducer has two or more laminated layers. It is preferable the case of a transducer having integral multiple of three, layers (3×m layers (m is an integer of 1 or more)).

Figure 23:
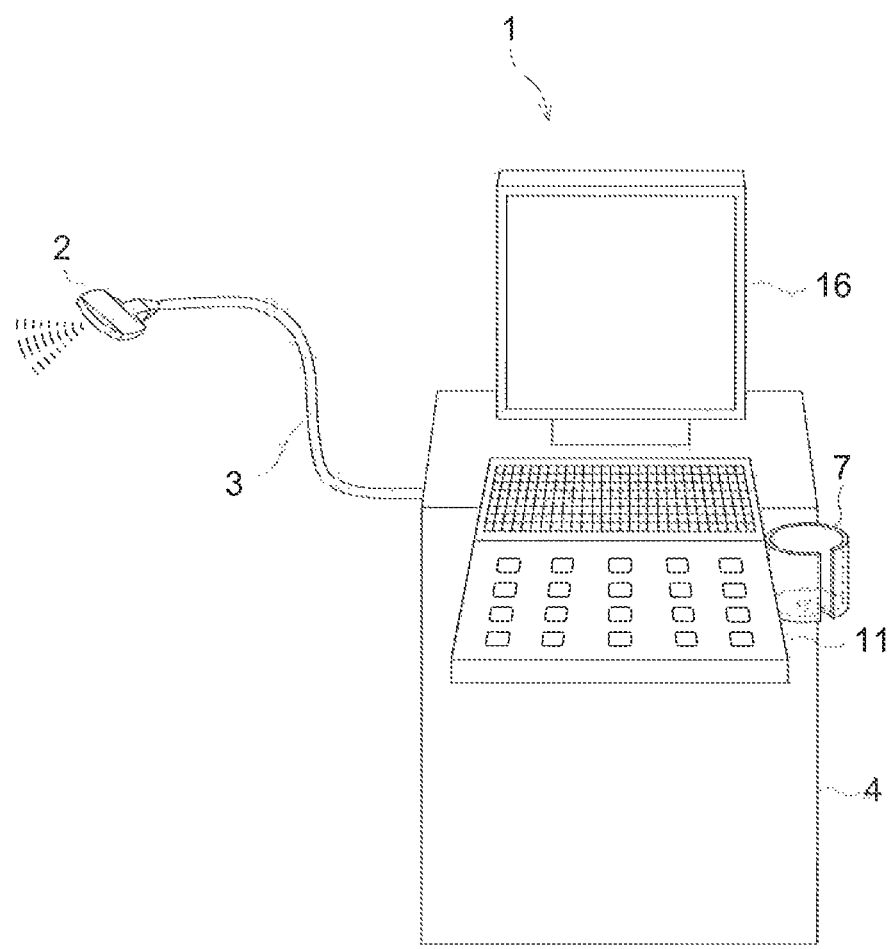
FIG. 23 is a perspective diagram showing the appearance composition of the ultrasound diagnostic imaging apparatus according to the present embodiment.

The laminated piezoelectric transducer constituted as mentioned above is used for the ultrasound transducer of an ultrasound probe, and the ultrasound diagnostic imaging apparatus as the example of this invention is constituted. As shown in FIG. 23, this ultrasound diagnostic imaging apparatus 1 is equipped with an Ultrasound probe 2 and a main body 4 of diagnostic apparatus, and these are connected through a cable 3. The ultrasound probe 2 transmits an ultrasound (transmitted ultrasound) to a test object such as a living body which is not illustrated and receives the ultrasound (reflected ultrasound) reflected from the test object. In this embodiment, Ultrasound probe 2 arranges two or more Ultrasound transducers 21 in the form of a one-dimensional array. The main body 4 of diagnostic apparatus makes Ultrasound probe 2 to transmit an ultrasound by transmitting an electrical transmission signal through a cable 3, and makes an image of an internal state in the test object as a cross-sectional imaging based on the received signal converted from the ultrasound received by Ultrasound probe 2.

The main body 4 of the ultrasound diagnostic apparatus comprises an Operation input unit 11 and Display unit 16. Operation input unit 11 comprises switches, buttons, track ball, mouse, and key board which are used to input various commands to start diagnosis or data such as personal information on the test object. The support picture for operation according to Operation input unit 11 and the ultrasonic imaging created based on the received signal are displayed in Display unit 16. Moreover, the Holder 7 which holds the ultrasound probe 2 at the un-using time is prepared at the proper place of Operation input unit 11 or the main body 4 of diagnostic apparatus.

Figure 24:
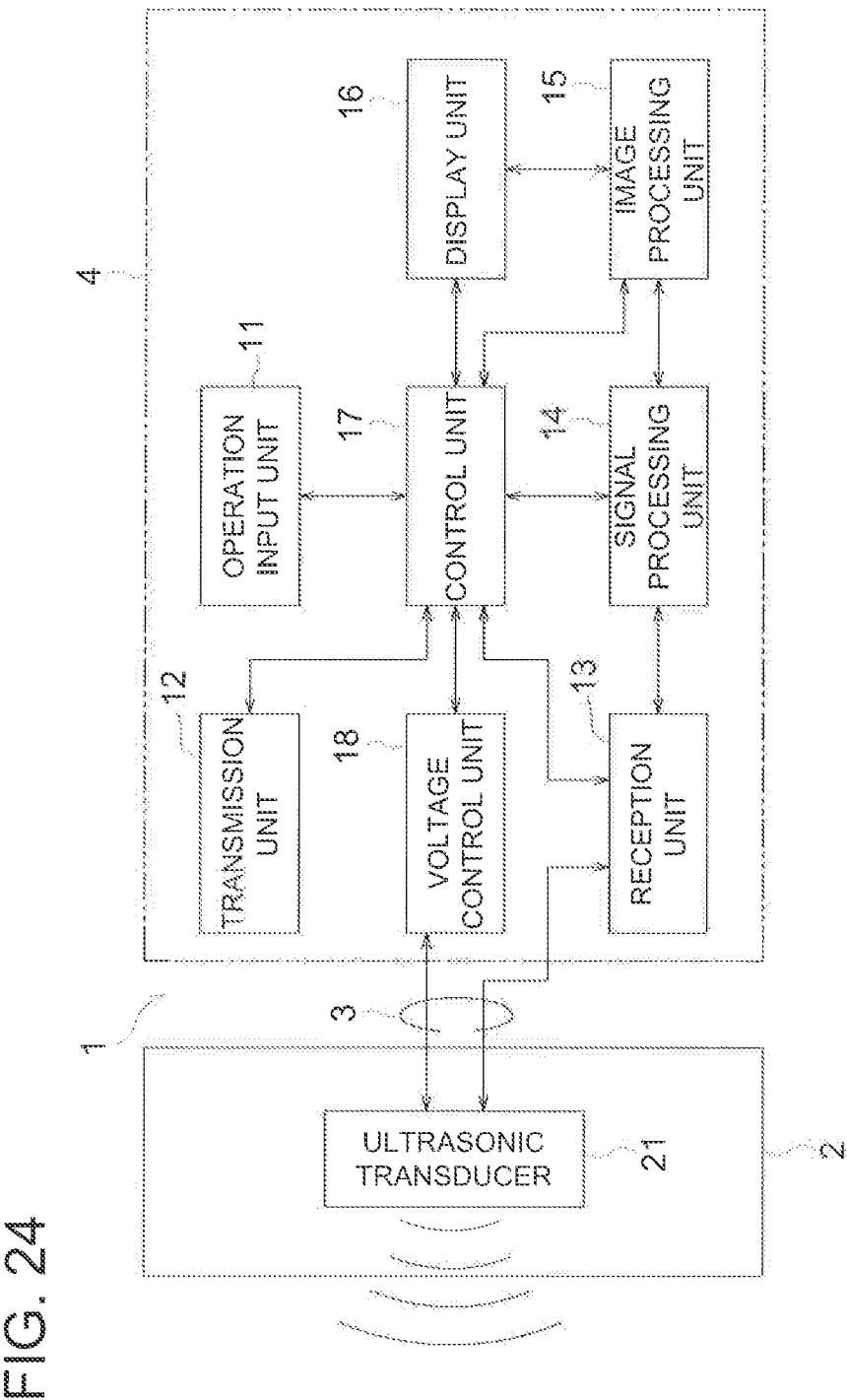
FIG. 24 is a block diagram showing the functional composition of the main body of diagnostic apparatus.

FIG. 24 is a block diagram showing the functional constitution of the main body 4 of diagnostic apparatus. The main body 4 of diagnostic apparatus comprises a Transmission unit 12, a Reception unit 13, a Signal processing unit 14, an Image-processing unit 15, a Control unit 17, and a Voltage control unit 18 in addition to Operation input unit 11 and Display unit 16 mentioned above.

Transmission unit 12 is a circuit which generates the transmission pulse as a transmission signal to Ultrasound probe 2 according to control of Control unit 17. Transmission unit 12 outputs a transmission pulse to Voltage control unit 18 through Control unit 17. An amplitude of a transmission pulse is amplified in Voltage control unit 18, and a transmission pulse is transmitted to the Ultrasound probe 2. Ultrasound probe 2 outputs the transmission ultrasound according to the received transmission pulse. Transmission unit 12 forms a transmission beam so that the transmission ultrasound from each Ultrasonic transducer 21 may focus at a predetermined focus position. In addition, an above-mentioned transmission ultrasound may consist of a plurality of coded pulses for which the above transmission ultrasound is elongated to the time base direction.

According to control of Control unit 17, Receiving unit 13 is a circuit which receives the received signal of an electrical signal through Cable 3 from Ultrasound probe 2, and outputs this received signal to Signal processing unit 14.

Signal processing unit 14 detects a reflection ultrasound from the output of Receiving unit 13. In addition, it may have a filter which extracts only the 3rd or more harmonic component.

Image-processing unit 15 is a circuit which generates the data (ultrasonic image data) of the imaging of the internal state of the test object based on the received signal processed in Signal processing unit 14 according to control of Control unit 17.

Display unit 16 is an equipment which displays the ultrasonic imaging of a test object based on the ultrasonic image data generated in Image-processing unit 15 according to control of Control unit 17. Display unit 16 is realized by display equipment such as CRT (Cathode-Ray Tube), LCD (Liquid Crystal Display), organic electroluminescence (Electronic Luminescence) display and plasma display, or printing equipment such as a printer.

Control unit 17 is a circuit equipped with a microprocessor, a storage element, and peripheral circuit thereof, and performs control of the whole ultrasonic diagnostic imaging apparatus 1 by controlling Operation input unit 11, Transmission unit 12, Voltage control unit 18, Reception unit 13, Signal processing unit 14, image-processing unit 15, and Display unit 16 according to the function concerned, respectively.

Figure 25:
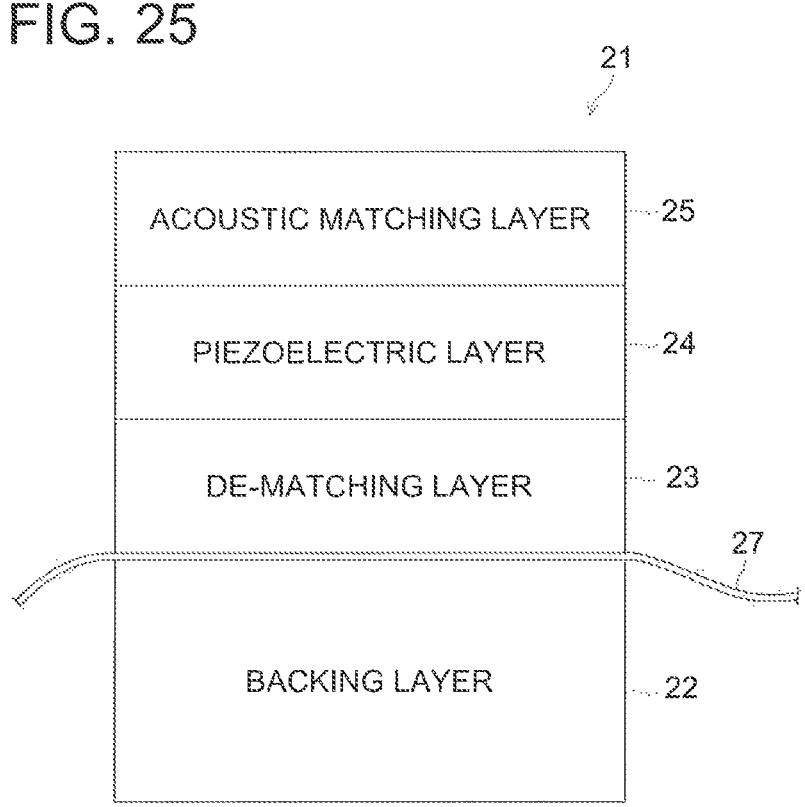
FIG. 25 is a schematic sectional drawing showing the structure of an ultrasound transducer.

As shown in FIG. 25, from the bottom of the figure, Ultrasonic transducer 21 is constituted by laminating the backing (back) layer 22, the de-matching layer 23, the piezoelectric material layer 24, and the acoustic matching layer 25. In addition, it may laminate an acoustic lens above the acoustic matching layer 25 if needed.

The backing layer 22 is an ultrasound absorber which supports the piezoelectric material layer 24 and may absorb an unnecessary ultrasound wave. That is, the backing layer 22 is prepared on the opposite side of the piezoelectric material layer 24 which transmits and receives art ultrasound wave to the test object, and absorbs the ultrasound wave which generates from the opposite direction of the test object and reaches to the backing layer 22. In addition, in the present embodiment, it may also be a institution without the backing layer 22.

As a backing material for the backing layer 22, employable are thermoplastic resins such as vinyl chloride, polyvinyl butyral (PVB), ABS resin, polyurethane (PUR), poly vinyl alcohol (PVAL), polyethylene (PE), polypropylene (PP), polyacetal (POM), polyethylene terephthalate (PETP), fluorine resin (PTFE), polyethylene glycol, and polyethylene terephthalate-polyethylene glycol glycol copolymer; press-molded composite materials in which powder such as tungsten oxide, titan oxide or ferrite is filled into natural robber, ferrite robber, epoxy resin or silicone resin; and materials in which composite material is pulverized and mixed with above described thermoplastic resin or epoxy resin and hardened, in order to adjust acoustic impedance, inorganic material such as MACOR glass or porous material having void, can also be employable.

As backing materials, rubber based composite material and/or epoxy based composite material is preferably used. Shape thereof may be selected appropriately according to a shape of a piezoelectric material layer 24 or a probe head 2 having thereof.

The de-matching layer 23 comprises a material having larger acoustic impedance than the piezoelectric material layer 24, and reflects the ultrasound wave outputted to the opposite direction of a test object to the piezoelectric material layer 24. Any material may be applicable as a material applied to the de-matching layer 23, as long as it has a large difference of the acoustic impedance between the piezoelectric material layer 24 and the de-matching layer 23, such as tungsten, or a tantalum, but tungsten carbide is preferable. Moreover, a mixed material with tungsten carbide and other materials is applicable. In the present embodiment the sensitivity to the transmission-and-reception of the ultrasound wave in the piezoelectric material layer 24 can be further enhanced by constituting the de-matching layer 23.

With reference to FIGS. 8, 9, 12, 16, 20, and 22, the above mentioned laminated piezoelectric material is applied to the piezoelectric material layer 24.

Specific examples of laminated piezoelectric materials include: conventionally used inorganic piezoelectric materials, such as a rock crystal, a piezoelectric ceramics PZT, PZLT, and thin film such as piezoelectric single crystal PZN-PT, PMN-PT, $LiNbO_3$, $LiTaO_3$, $KNbO_3$, ZnO, and AlN; and organic piezoelectric materials such as polyvinylidene fluoride or polyvinylidene fluoride based copolymer, polyvinylidene cyanide based copolymer or cyanidation vinylidene based copolymer, odd number nylon such as nylon 9 and nylon 11, aromatic nylon, aliphatic nylon, polylactic add, polyhydroxy carboxylic acid such as poly hydroxy butylate cellulose derivatives, or poly urea. Further, included is a composite material in which an inorganic piezoelectric material and an organic piezoelectric material, or an inorganic piezoelectric material and organic high polymer material are used in combination.

The layer thickness of one layer of the laminated piezoelectric material is preferably in the range, of 5-200 μm in view of workability, although depending on the predetermined center frequency (wavelength λ). Since each piezoelectric material has mutually equal thickness, it becomes easy to manufacture each piezoelectric material, resulting in enhancing the productivity of the ultrasound transducer 21.

As for a method of forming the piezoelectric material layer comprising organic piezoelectric material, it is preferable a method of forming a film by coating or a method of forming a film by vacuum evaporation (vapor deposition polymerization). Specific example of the above-mentioned coating method includes: a spin coating method, a solvent casting method, a melt casting method, a melt pressing method, a roll coating method, a flow coating method, a printing method, a dip coating method, or a bar coating method. Further, in a vacuum evaporation (vapor deposition polymerization) method, a film can be obtained by evaporating a monomer from a single or a plurality of evaporation sources in vacuum degree of about hundreds Pa or less, and depositing and reacting on a substrate. Temperature adjustment of a substrate is performed suitably if needed.

In the formation of the electrode, a layer of a metal such as titanium (Ti) or chromium (Cr) is formed according to a sputtering method as an under layer to obtain a thickness of from 0.02 to 1.0 μm. Then, metal materials composed mainly of the metal elements described above or metal materials composed of alloys thereof, and optionally insulation materials are deposited according to a sputtering method or another appropriate method to form a 1 to 10 μm thick layer. Then, the polarization treatment of the above-mentioned piezoelectric material layer (piezoelectric material film) is performed. As the above-mentioned metal material, used are gold (Au), platinum (Pt), silver (Ag), palladium (Pd), copper (Cu), nickel (Ni), or tin (Sn). The electrode formation can be carried out by a screen printing method, a dipping method or a melt splaying method employing a conductive paste in which fine metal particles are mixed with a low melting point glass.

FPC (Flexible Printed Circuits) 27 is sandwiched between the backing layer 22 and the de-matching layer 23, and the transmitted signal from Voltage control unit 18 is applied to the piezoelectric material layer 24 by this FPC 27. Moreover, the received signal generated in the piezoelectric material layer 24 is applied to Receiving unit 13 by FPC 27.

Figure 26:
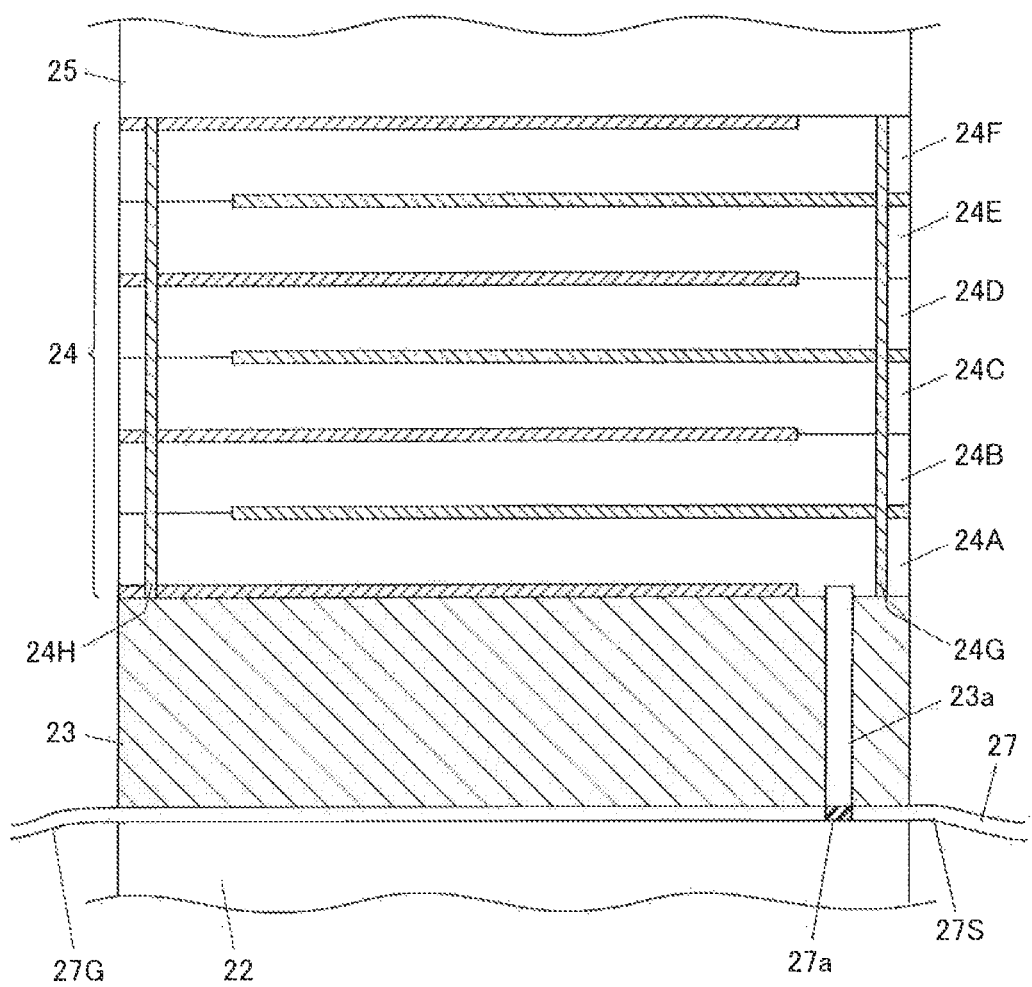
FIG. 26 is a sectional drawing explaining the specific structure of the piezoelectric material layers shown in FIG. 25.

Hereinafter, an example of the piezoelectric material layer 24 with reference to FIG. 26 will be explained. Herein, in the example shown in FIG. 26, the 6-layer piezoelectric material shown in FIG. 22 is applied.

The piezoelectric material layer 24 is constituted by laminating the piezoelectric materials 24A-24F. The electrode is provided both sides in thickness direction of each piezoelectric materials 24A-24F, respectively. Specifically, the electrode is provided, on the under surface of the piezoelectric materials 24A, 24C, and 24E and on the upper surface of the piezoelectric materials 24B, 24D, and 24F from the left end pair to right end part in the figure except for the fixed length from the right end part. On the other hand, the electrode is provided on the under surface of the piezoelectric materials 24B, 24D, and 24F and on the upper surface of the piezoelectric materials 24A, 24C, and 24E from the right end part to left end part in the figure except for fixed length from the left end part.

Since piezoelectric materials 24A-24F are laminated as mentioned above, the electrode on the countered surface on the adjacent piezoelectric materials each other mutually is contacted.

Moreover, at the neighborhood of both right end and left end of the piezoelectric material layer 24, the conductive parts 24G and 24H are formed, respectively, from the top end to the bottom end. The conductive part 24G forms the electrical connection of the electrode arranged only at the neighborhood of the right end part of the piezoelectric material layer 24. The conductive part 24H forms the electrical connection of the electrode arranged only the neighborhood of the left end part of the piezoelectric material layer 24.

The de-matching layer 23 of the present embodiment is formed with a conductive material, and a slit 23a is provided on the neighborhood of right end and from top end to the bottom end in the figure. That is, the left-hand side portion and the right-hand side portion of the de-matching layer 23 is insulated by the slit 23a. Herein, in the following description, a right-hand side portion may be referred to as a signal portion, and a left-hand side portion as a ground portion.

The signal line 27S and the ground line 27G are formed on FPC 27 with sandwiching the insulated part 27a. The insulated part 27a is arranged at the position corresponding to the slit 23a of the de-matching layer 23. Therefore, the signal line 27S of FPC 27 is electrically connected to the signal portion of the de-matching layer 23, and the ground line 27G of FPC 27 is electrically connected to the ground portion of file de-matching layer 23.

Since, the ultrasound transducer 21 is constituted as mentioned above, it has the composition that the piezoelectric materials 24A-24F are mutually in the electrically parallel connection.

An acoustic matching layer 25 junctions to match acoustic impedances between a piezoelectric material layer 24 and a test object, and to control reflection at interface. The acoustic matching layer 25 is provided on a test object side of piezoelectric material layer 24, where corresponds to a direction of transmission and reception of ultrasound wave. The acoustic matching layer 25 has intermediate acoustic impedance between the piezoelectric material layer 24 and the test object.

As materials for acoustic matching layer 25, employable are aluminum, aluminum alloy (for example, Al—Mg alloy), magnesium alloy, MACOR glass, glass, fused quartz, copper graphite, PE (polyethylene), PP (polypropylene), PC (polycarbonate), ABC resin, ABS resin, AAS resin, AES resin, nylon (PA6, PA6-6), PPO (polyphenylene oxide), PPS (polyphenylene sulfide: also applicable with glass fiber), PPE (polyphenylene ether), PEEK (polyether ether keton), PAI (polyamide imide), PETP (polyethylene terephthalate), epoxy resin paid urethane resin. It is preferable to employ a molded material comprising a thermosetting resin such as epoxy resin by adding filler such as zinc flower, titan oxide, silica, alumina, colcothar, ferrite, tungsten oxide, ytterbium oxide, barium sulfate, tungsten, and molybdenum.

Acoustic matching layer 33 may be constituted in a single layer or a plurality of layers, preferable in 2 or more layers, more preferable in 4 or more layers. Thickness of acoustic matching layer 25 has to be determined to satisfy to be $\lambda/4$, provided that a wave length of ultrasound is $\lambda$. Thus, total thickness of the acoustic matching layer is generally about in a range of 20-500 μm.

In the present embodiment, used is the acoustic matching layer 25 constituted as shown in FIG. 27, for example. That is, the acoustic matching layer 25 is formed by a multiple coating of 5 layers in the thickness direction. As will be described below, acoustic impedance is adjusted by changing material composition on each layer respectively, and performing a weighting of the acoustic impedance in the thickness direction.

For the uppermost layer of the acoustic matching layer 2, thickness is set to be 10 μm and used is YE5822 produced by Momentive Performance Materials as a base material, incorporating 40 wt % of zinc oxide as a filler, whereby acoustic velocity is set to be 900 m/s and specific gravity is set to be 1.45 g/cm$^3$, and acoustic impedance is set to be 1.3 MRayl.

For the 2nd layer, thickness is set to be 10 μm and used is EVA (ethylene vinyl acetate copolymer resin) as a base material, whereby acoustic velocity is set to be 2,000 m/s and specific gravity is set to be 0.9 g/cm$^3$, and acoustic impedance is set to be 1.8M Rayl.

For the 3rd layer, thickness is set to be 10 μm and used is EP007 produced by CEMEDINE Co. Ltd, as abase material, whereby acoustic velocity is set to be 2,300 m/s and specific gravity is set to be 1.1 g/cm$^3$, and acoustic impedance is set to be 2.5 MRayl.

For the 4th layer, thickness is set to be 10 μm and used is C-1001A/B produced by TESL Co. Ltd., as a base material, whereby acoustic velocity is set to be 2,500 m/s and specific gravity is set to be 1.2 g/cm$^3$, and acoustic impedance is set to be 3.0 MRayl.

For the lowermost layer, thickness is set to be 10 μm and used is C-1001A/B produced by TESL Co. Ltd., as a base material, incorporating 15 wt % of tungsten trioxide as a filler, whereby acoustic velocity s is set to be 2,300 m/s and specific gravity is set to be 1.5 g/cm$^3$, and acoustic impedance is set to be 3.5 MRayl.

In addition, a direction of a weighting of the acoustic impedance in the acoustic matching layer 25 is not limited to the thickness direction but it may be horizontal direction as well.

In the present embodiment, the piezoelectric material layer 24 mentioned above constitutes the ultrasound transducer 21, whereby when setting a wavelength of the ultrasound wave (fundamental frequency component) at transmission and reception to be λ, the piezoelectric material layer 24 can perform 3λ/4 resonance, can extract the 3rd resonance component of wavelength λ (third harmonic component generated in the living body) by high gain, and can reduce a primary resonance component (fundamental frequency component). Therefore, it is possible to be unnecessary to use the filter and amplifier in the reception unit 13. Or in the case of using these lifter or amplifier, order of a filter can be made low or the gain of amplifier can be made small.

In addition, in the present embodiment, the inorganic piezoelectric material layer formed with the inorganic piezoelectric material may be further laminated and the resulting inorganic piezoelectric material layer may be used to transmit an ultrasound wave. At this time, the organic piezoelectric material layer 24 mentioned above may be applied to reception of the ultrasound wave.

Specific preparation method and the material of the ultrasound probe 2 equipped with the piezoelectric material layer 24 which performs 3λ/4 resonance mentioned above will be detailed. Herein, the following description includes the preparation methods of the piezoelectric material layer 24 above mentioned with reference to FIG. 22.

At first, a fixed plate, a backing layer, and a patterned FPC were laminated sequentially from the lower layer. A lamination adhesion was performed by using epoxy adhesive DP-460 produced by 3M, under the pressure of 30 kgf/cm², at 50° C. for 4 hours.

Next, a 20 μm film was prepared by a casting method in which MEK (methyl ethyl ketone) is used for solvent for P(VDF-TrFE) having composition ratio to VDF:TrFE=3:1. A plasma treatment or a wet processing may be performed in order to enhance an adhesive property to the prepared film. In the wet processing, for example, Tetra etch (registered trademark) can be used. After performing annealing treatment for 1 hour at 135° C. to the film prepared as mentioned above, oxygen plasma treatment was performed. Then, the electrode was patterning in 0.1 μm of Cr as a ground and subsequently set to 0.2 μm of Au. Next, a poling process to the film on which electrode patterning was performed, thereby the piezoelectric material was prepared which has the electromechanical coupling coefficient (kt) of 0.25.

Figure 28A:
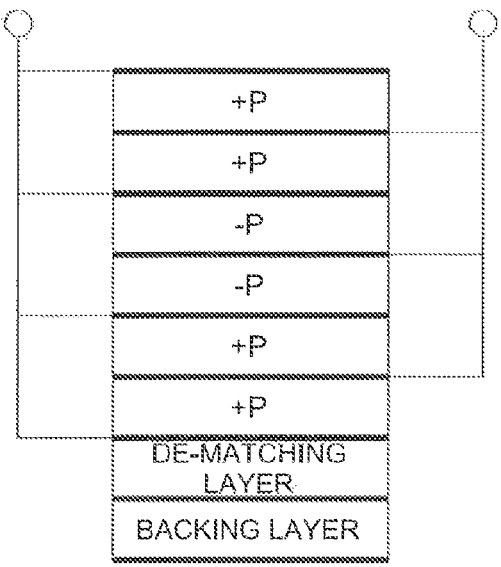
FIGS. 28a, 28b and 28c are figures explaining the composition of an ultrasound transducer of the present embodiment and a comparative example.

Then, 6 layers of piezoelectric materials prepared as mentioned above were laminated. At this time, as shown in FIG. 28a, 6 piezoelectric materials were laminated so that the direction of polarization from the 2nd layer to the top layer in the 6 piezoelectric materials were the sane direction, an opposite direction, an opposite direction, the same direction and the same direction as the that of lowermost piezoelectric material, and pasted up by epoxy adhesive DP-460 produced by 3M company.

Then, the through hole with a bore diameter of 0.15 mm was established at near the both ends of the laminated piezoelectric material in width direction by intervals of 0.2 mm in the direction perpendicular to a width direction (azimuth direction). A plating treatment was performed to the established through hole, and the electrically connecting part mentioned above was formed.

Next, the resulting laminated piezoelectric material was pasting up on the tungsten carbide formed in a plate form having a thickness of 50 μm which functions as a de-matching layer. Then, this was cut into a size of 42.5 mm×5.6 mm. The slit was prepared on tungsten carbide in order to isolate between a signal portion (right-hand side portion) and a grand portion (left-hand side portion).

After forming an acoustic matching layer in the tipper surface of a laminated piezoelectric material as it mentioned above with reference to FIG. 27, the backing layer which FPC pasted up as mentioned above were laminated and pasted up with the laminated piezoelectric transducer formed on the upper surface. Then it was dicing at intervals of 0.2 mm to an azimuth direction, and elementized, a plurality of ultrasound transducers 21 were formed. In addition, for making element, it is not limited to dicing, but a laser processing may be applicable, for example. The ultrasound probe was prepared by applying the ultrasound transducer formed as mentioned above, and it was referred to as Example 5.

Figure 28B:
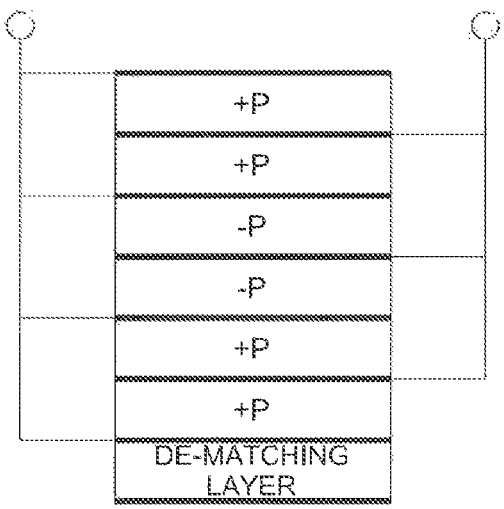

Then, prepared was the ultrasound probe as shown in FIG. 28b which eliminated a de-matching layer from the ultrasound probe of Example 5 prepared as mentioned above. It was referred to as Comparative example 1.

Figure 28C:
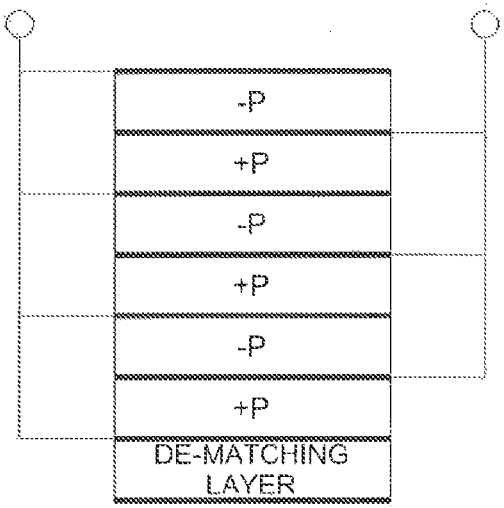

Furthermore, prepared was an ultrasound probe as shown in FIG. 28c, in which 6 piezoelectric materials of the ultrasound probe of the comparative example 1 were laminated so that the direction of polarization from the 2nd layer to the top layer in the 6 piezoelectric materials were an opposite direction, the same direction, an opposite direction, the same direction and an opposite direction as the that of lowermost piezoelectric material. It was referred to as Comparative example 2.

Figure 29:
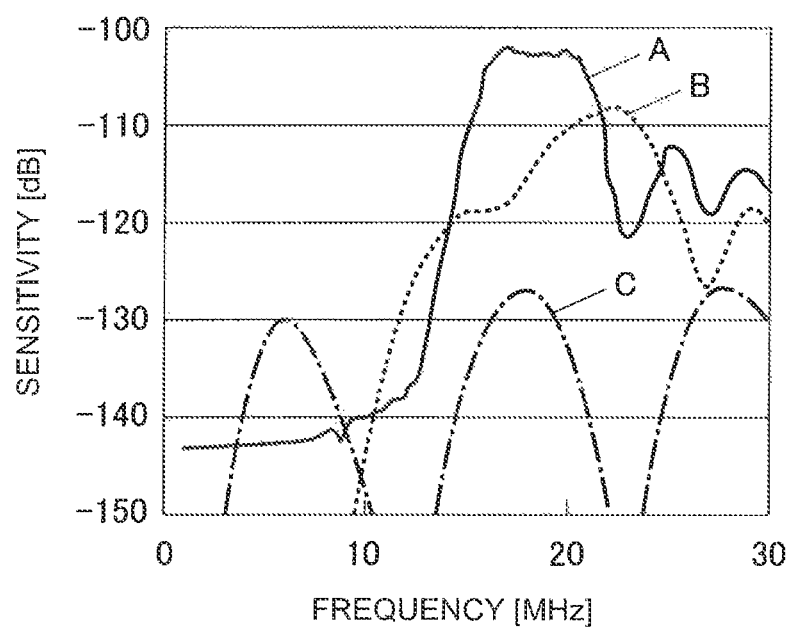
FIG. 29 is a graph showing experimental data and a simulation result about the transmission-and-reception characteristics of the ultrasound by each piezoelectric transducer of FIGS. 28a, 28b and 28c.

About the ultrasound probe of Example 5, Comparative example 1, and Comparative example 2 prepared as mentioned above, the respectively, Pulsar Receiver (PANAMETRICS-NDT MODEL 5900PR, produced by Olympus Corp., input impedance of 5,000Ω) and Oscilloscope (TPS5032, product made by Tektronix) was connected. The ultrasound probe was put into the degassed water, and metal reflecting plates have been arranged to the acoustic emission side. The received ultrasound wave was changed into the electrical signal, and checked the voltage waveform with the oscilloscope. The alignment with an ultrasound probe and a reflecting plate was determined with the coordinate where the effective value of the voltage waveform showed the peak. Transmission and reception of the ultrasound wave were performed after alignment, and transmission and reception, sensitivity was measured. The result is shown in FIG. 29. A, B and C respectively represents Example 5, Comparative example 1 and Comparative example 2.

As shown in FIG. 29, it is found that in the ultrasound probe of Example 5, the sensitivity at a peak improves by 6 dB compared with the ultrasound probe of Comparative example 1, and the sensitivity of a peak improves by 25 dB compared with the ultrasound probe of Comparative example 2. Moreover, in the ultrasound probe of Example 5, no peak was noticed at near 6 MHz which corresponds to λ/4 resonance frequency, and it means that peak for λ/4 resonance is suppressed. Further, it was found that at near 18 MHz which corresponds to 3λ/4 resonance frequency, the sensitivity is extremely improved compared with the ultrasound probe of Comparative example 1 and Comparative example 2.

As explained above, according to the embodiment, of the present invention, the piezoelectric material layer 24 has an electrode on the surface of the piezoelectric materials 24A-24F of between the layer and both ends, and an electrical signal is output and input via these electrodes. The piezoelectric materials 24A-24F have remanent polarization in the thickness direction respectively. The relationship between the direction of an electric displacement or an electric field by the direct piezoelectric effect and a direction of remanent polarization or a crystal axis is arranged so that it may have the following periodicity: the relationship of the (4P+1)th layer piezoelectric materials 24A and 24E from the fixed end is used as the basic relationship, the relationship of the (4P+2)th and (4P+3)th layer piezoelectric materials 24B, 24C and 24F adjacent thereto is arranged to have a opposite relationship to the basic relationship, and the (4P+4)th piezoelectric material 24D thereon may be arranged to have the same relationship as the basic relationship. The de-matching layer 23 with larger acoustic impedance than the piezoelectric material layer 24 for reflecting vibration spread from the piezoelectric material layer 24 to the fixed-end side is formed in the fixed-end side of the piezoelectric material layer 24. As a result, output sound pressure at the time of transmission of a required higher resonance component or output voltage at the time of reception can be made larger than those of the primary resonance component, and high sensitive detection can be attained. Moreover, much more high sensitive detection can be attained by a de-matching layer.

Moreover, according to the embodiment of the present invention, the piezoelectric material layer 24 has an electrode on the surface of the piezoelectric materials of between the layers and both ends, and an electrical signal is output and input via these electrodes. The piezoelectric materials have remanent polarization in the thickness direction respectively. The relationship between the direction of an electric displacement or an electric field by the direct piezoelectric effect and a direction of remanent polarization is arranged so that it may have the following periodicity: the relationship of the (8P+1)th layer piezoelectric material adjacent to the fixed end is used as the basic relationship, the relationship of the (8P+2)th layer piezoelectric material adjacent thereto is arranged to have the same relationship as the base, and the (8+3)th, (8P+4)th, (8P+5)th, and (8P+6)th piezoelectric material each may be arranged to have an opposite relationship to the basic relationship, and (8P+7)th and (8P+8)th layer piezoelectric materials thereon may be arranger to have the same relationship. The de-matching layer 23 with larger acoustic impedance than the piezoelectric material layer 24 for reflecting vibration spread from the piezoelectric material layer 24 to the fixed-end side is formed in the fixed-end side of the piezoelectric material layer 24. As a result, output sound pressure at the time of transmission of a required higher resonance component or output voltage at the time of reception can be made larger than those of the primary resonance component, and high sensitive detection can be attained. Moreover, much more high sensitive detection, can be attained by a de-matching layer.

Further, according to the embodiment of the present invention, two electrodes each located at outermost side of adjacent piezoelectric material 24A-24F are connected in an electrically parallel connection, thereby capacitance of a piezoelectric layer can be enlarged, electrical impedance can be reduced, resulting in improving the impedance matching at the time, of connecting an electric circuit to the latter part.

Further, according to the embodiment of the present invention, the piezoelectric material layer 24 is formed by laminating 3×m layer of the piezoelectric material (m is an integer of 1 or more). As a result, the vibration mode of each piezoelectric material can be understood by coding by coinciding the boundary of piezoelectric materials with the node and antinode of an elastic wave of a piezoelectric material. Thereby, by setting up suitably direction of the remanent polarization of each piezoelectric material, while the sensitivity ma higher resonance component increases, a primary resonance component can be suppressed.

Further, according to the embodiment of the present invention, since the de-matching layer was formed including tungsten carbide, whereby reflection efficiency can be enhanced and the sensitivity of a piezoelectric layer can be enhanced further.

In addition, the description according to the embodiment of the present invention is an example of an ultrasound transducer, an ultrasound probe, and ultrasound diagnostic imaging apparatus concerning this invention and is not limited thereto. It can be changed suitably also about the details constitution of each functional unit and details operation which constitute an ultrasound transducer, an ultrasound probe, and ultrasound diagnostic apparatus.

Figure 30:
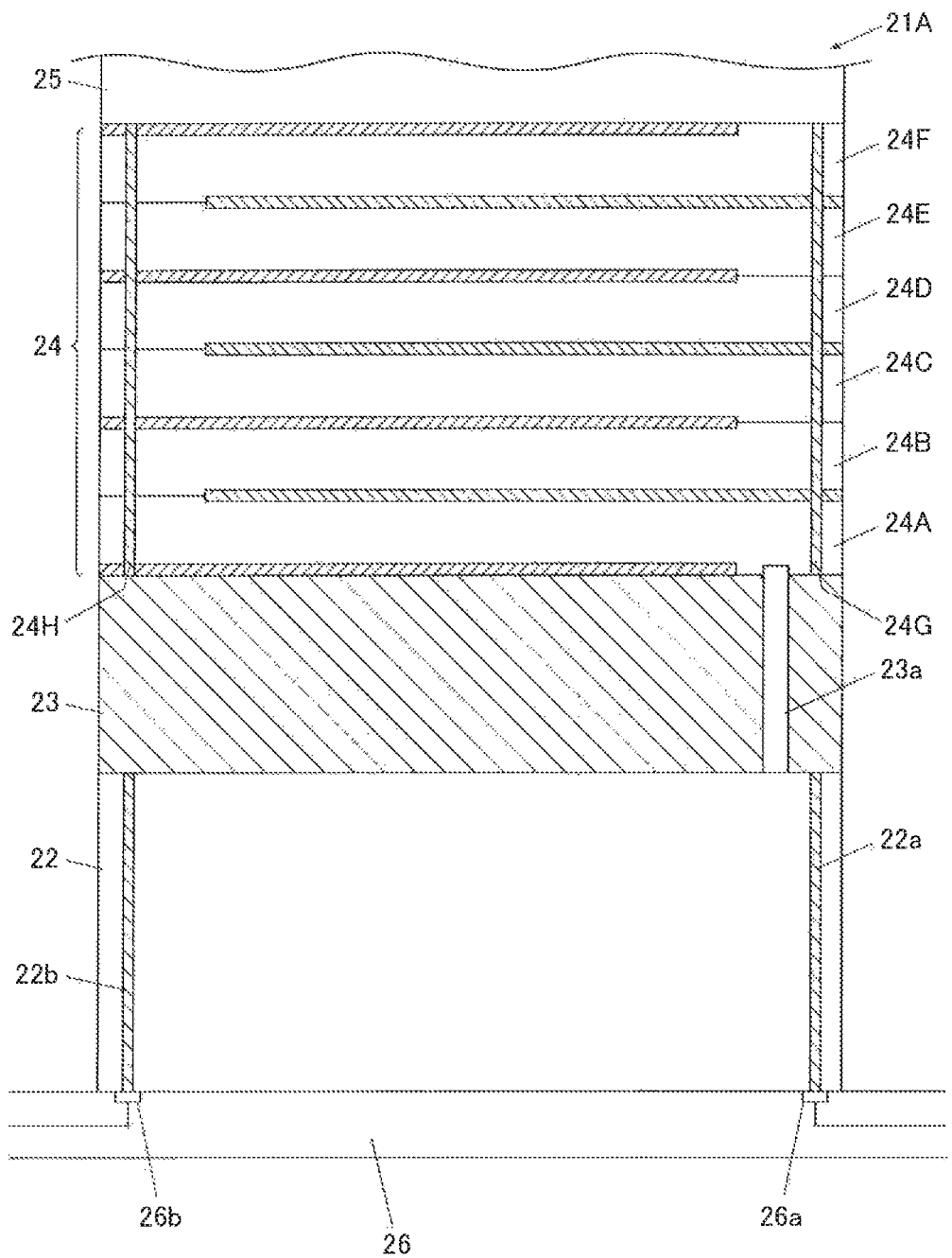
FIG. 30 is a sectional drawing explaining the example of other composition of an ultrasound transducer.

Moreover, according to the embodiment of the present invention, FPC 27 is prepared between the backing layer 22 and the de-matching layer 23 and the electrical signal is input and output to the piezoelectric material layer 24. For example, as shown in FIG. 30, FPC 27 may be replaced by a substrate 26 and the electrical signal may be input and output from this substrate 26 to the piezoelectric material layer 24. As specifically shown in FIG. 30, near both of right and left end of the backing layer 22, the conductive parts 22a and 22b are formed respectively from the upper end to the lower end. Moreover, on the undersurface of the backing layer 22, the substrate 26 on which the wiring pattern was formed is pasted by using predetermined adhesives. The substrate 26 has the terminal 26a connected to the signal line formed in the wiring pattern, and the terminal 26b connected to a ground line. Si (silicon) substrate or a glass epoxy substrate is applicable as the substrate 26, for example. One end of the conductive part 22a of the backing layer 22 contacts to the signal portion of a de-matching layer, and the other end contacts to the terminal 26a of the substrate 26. Moreover, one end of the conductive part 22b contacts to the ground portion, of a de-matching layer, and the other end is contacted to the terminal 26b of the substrate 26.

That is, according to the present embodiment, the substrate 26 is electrically connected with the electrodes and the predetermined wiring pattern is formed. The piezoelectric material layer 24 is attached in one with the substrate 26. As a result, since increase of wiring capacity can be controlled and the loss of a charge can be controlled, sensitivity can be improved.

Figure 31:
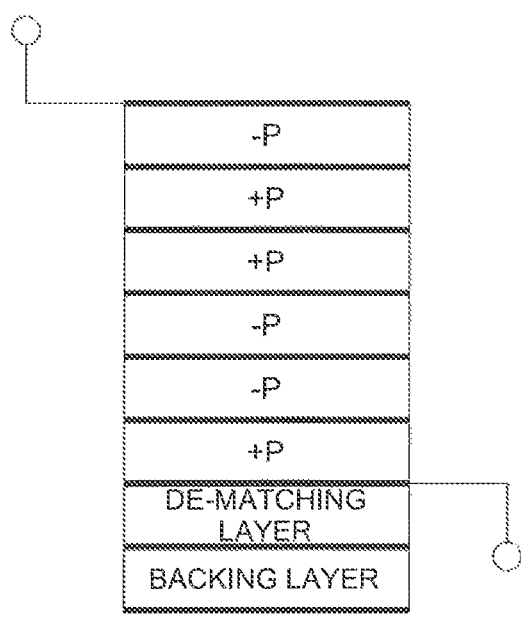
FIG. 31 is a figure explaining the example of other composition of an ultrasound transducer.

Moreover, according to the present embodiment, each piezoelectric material is not limited to be connected in electrically parallel, but the piezoelectric material connected in series may be applicable. For example, as shown in FIG. 31, electrodes are provided between the piezoelectric material layers and on both end surfaces of the laminated piezoelectric material. Terminals are connected to the electrodes of the piezoelectric material surface of the both ends of a piezoelectric layer in a series connection. As shown in FIG. 31, the relationship between the direction of an electric displacement or an electric field by the direct piezoelectric effect and a direction of remanent polarization or a crystal axis of the 1st layer piezoelectric material at the fixed end side where the de-matching layer is provided is used as the basic relationship, the 2nd and 3rd layer piezoelectric material adjacent thereto is arranger to have an opposite relationship to the basic relationship, the 4th or more layer piezoelectric material each is arranged to have the same relationship. Namely, the relationship between the direction of an electric displacement or an electric field by the direct piezoelectric effect and a direction of remanent polarization is arranged so feat it may have the following periodicity: the relationship of the (4P+1)th layer piezoelectric material (P is 0 or a positive integer) adjacent to the de-matching layer is used as the basic relationship, the relationship of the (4P+2)th and (4P+3)th layer piezoelectric material adjacent thereto is arranged to have a opposite relationship to the basic relationship, and the (4P+4)th piezoelectric material thereon may be arranged to have the same relationship as the basic relationship. According to this arrangement, it results that the sensitivity by $\lambda/4$ resonance is decreased more and the sensitivity by $3\lambda/4$ resonance is amplified more.

Figure 32:
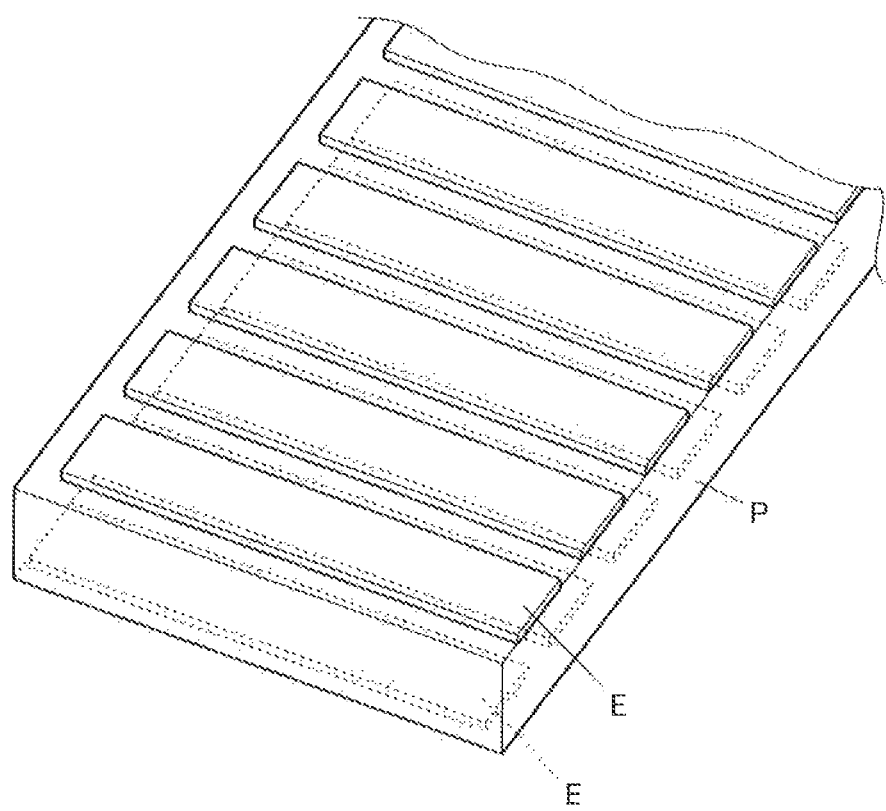
FIG. 32 is a figure explaining the example of other composition of an ultrasound transducer.

Further, according to the present embodiment, after laminating a plurality of piezoelectric materials, dicing was carried out to make elements. However, for example as shown in FIG. 32, an ultrasound probe, may be prepared by that patterning and the poling process of an electrode are carried out on the piezoelectric material P so that electrodes E may be arranged in array with, a sequence at a predetermined interval and a plurality of them are laminated by predetermined direction, resulting in without cutting the piezoelectric material by dicing. That is, according to the present embodiment a plurality of ultrasound transducers can be formed in array by forming electrode E is formed on the surface of the piezoelectric material P arranged in array with a sequence at a predetermined interval. As a result, it becomes no need to cutting to make elements and a depolarization caused by the heat and vibration at the time of cutting of a piezoelectric material can be prevented.

Moreover, according to the present embodiment, the piezoelectric materials 24A-24F are explained as the example in winch the de-matching layer is prepared at the fixed end side of the 6-layer laminated piezoelectric material layer 24. However, as will be described below, high sensitivity can be obtained in the embodiment in which the de-matching layer is prepared on the fixed end side of the 2-layer laminated piezoelectric layer.

Figure 33A:
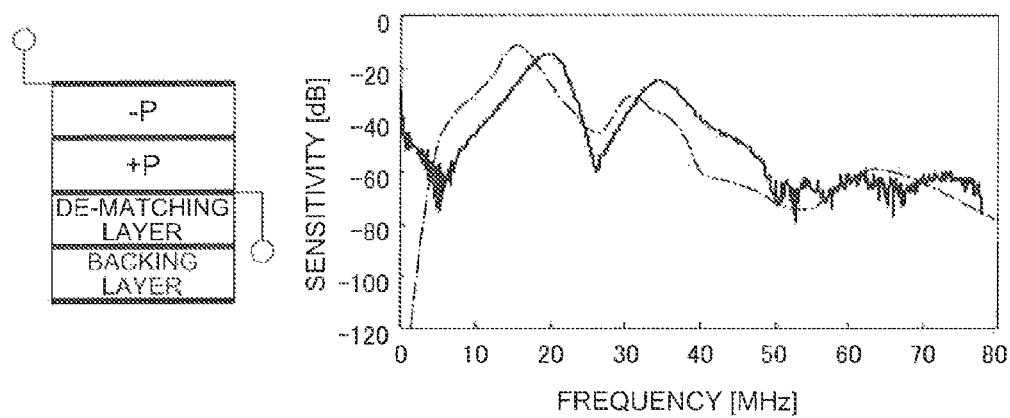
FIGS. 33a and 33b are graphs showing experimental data and a simulation result about the transmission-and-receptor characteristics of the ultrasound by the 2-layer piezoelectric transducer in electrically series connection.
Figure 33B:
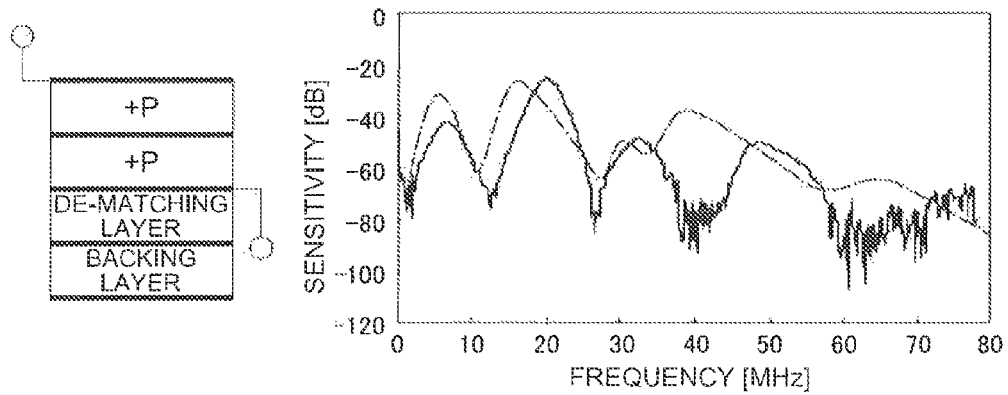

As shown in the left figure of FIG. 33a, when two layers of piezoelectric materials are laminated in electrically series connection and the direction of the remanent polarization of each piezoelectric material of the piezoelectric layer is set to an opposite direction mutually, and the transmission-and-reception of the ultrasound wave was carried out. The result as shown in the right figure of FIG. 33a was obtained. Moreover, as a comparative example, as shown in the left figure of FIG. 33b, the direction of the remanent polarization of each piezoelectric material of a piezoelectric-layer is set up to the same direction, mutually and the transmission-and-reception of the ultrasound wave was carried out. The result is shown in the right figure of FIG. 33b. Here, λ/4 resonance frequency of these piezoelectric layers is 6.5 MHz. Moreover, in FIG. 33, a solid line shows an experimental result and the chain line shows the simulation result.

As shown in FIG. 33a, when the direction of the remanent polarization of each piezoelectric material of the piezoelectric layer is set to an opposite direction mutually, a peak was not observed near 6.5 MHz which corresponds to resonance frequency, and peak for λ/4 resonance has disappeared. And it is found that sensitivity is improving by about 10 dB or more in near 19.5 MHz which corresponds to 3λ/4 resonance as compared with the result shown in FIG. 33b.

Figure 34A:
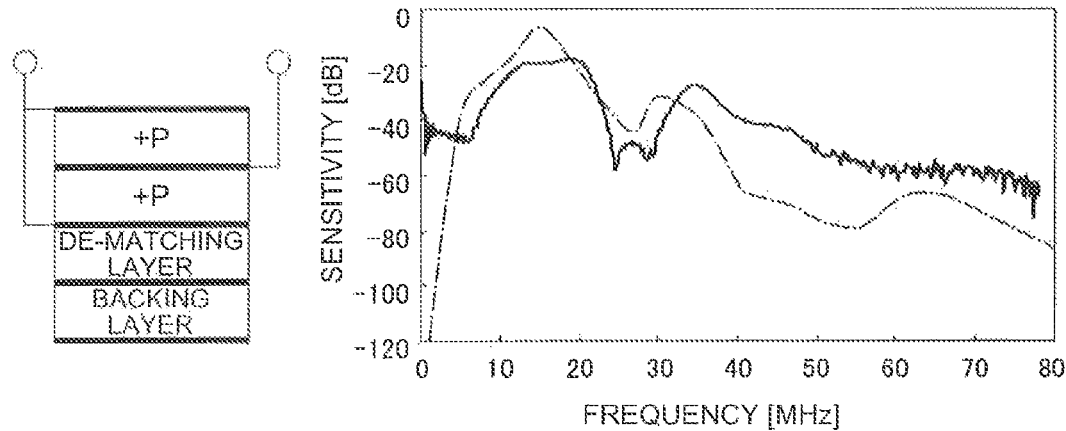
FIGS. 34a and 34b are graphs showing experimental data and a simulation result about the transmission-and-reception characteristics of the ultrasound by the 2-layer piezoelectric transducer in electrically parallel connection.
Figure 34B:
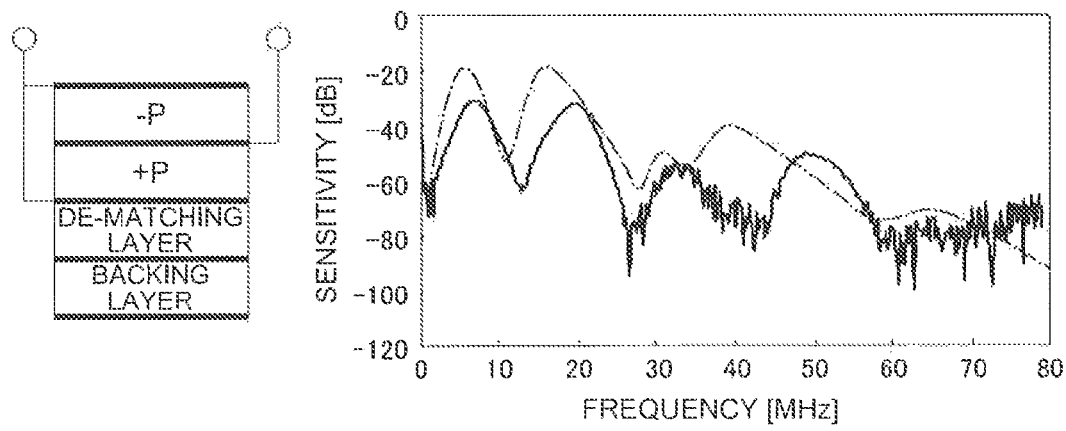

Moreover, as shown in the left figure of FIG. 34a, when two layers of piezoelectric materials are laminated in electrically parallel connection and the direction of the remanent polarization of each piezoelectric material of the piezoelectric layer is set to the same direction mutually, and the transmission-and-receptor; of the ultrasound wave was carried out. The result as shown in the right figure of FIG. 34a was obtained. Moreover, as a comparative example, as shown in the left figure of FIG. 34b, the direction of the remanent polarization of each piezoelectric material of a piezoelectric layer is set to an opposite direction mutually and the transmission-and-inception of the ultrasound wave was carried out. Tire result is shown in the right figure of FIG. 34b. Here, λ/4 resonance frequency of these piezoelectric layer's is 6.5 MHz. Moreover, in FIGS. 34a and 34b, a solid line shows an experimental result and the chain line shows the simulation result.

As shown in FIG. 34a, when the direction of the remanent polarization of each piezoelectric material of the piezoelectric layer is set to the same direction mutually, a peak was not observed near 6.5 MHz corresponding to resonance frequency, and λ/4 resonance, peak has disappeared. And it is found that sensitivity is improving by about 20 dB or more in near 19.5 MHz which is λ/4 resonance as compared with the result shown in FIG. 34b.

According to the present embodiment described was the example of improving the sensitivity at λ/4 resonance frequency, but it is not limited thereto. It may also constitute the case in which the sensitivity is enhanced when the resonance frequency is odd times (3 or more times) of λ/4, such as 5λ/4.

Moreover, the structure of the piezoelectric layer in the present embodiment may be a composite structure besides what is called monolithic structure, or it may be a structure in which thickness has a distribution in order to perform a weighting horizontally, for example, as described in U.S. Pat. No. 6,691,387.

DESCRIPTION OF THE ALPHANUMERIC DESIGNATIONS

1: Ultrasound diagnostic imaging apparatus
2: Ultrasound probe
13: Receiving unit
15: Image-processing unit
21: Ultrasound transducer
23: De-matching layer
24: Piezoelectric layers (laminated piezoelectric transducer)
24A-24F: Piezoelectric material
22: Substrate (wiring board)

What is claimed is:

1. An ultrasound transducer comprising:
a laminated piezoelectric material having n piezoelectric material layers, where n is an integer of 3 or more, each having an equal thickness, and electrodes between the piezoelectric material layers and on both end surfaces of the laminated piezoelectric material for input and output of an electrical signal, each of the piezoelectric material layers having a remanent polarization in a thickness direction, and
a de-matching layer provided on an opposite surface side of a transmission of an ultrasound wave, wherein the de-matching layer has a larger acoustic impedance than the laminated piezoelectric material and reflects a vibration propagated from the laminated piezoelectric material to the de-matching layer side,
wherein the ultrasound transducer resonates by a thickness stretch of the piezoelectric materials,
a relationship between a direction of an electrical displacement by the direct piezoelectric effect or a direction of an electrical field of a piezoelectric material generated by a voltage applied to the electrodes and a direction of the remanent polarization in the (4P+1)th layer from the de-matching layer side, where P is 0 or a positive integer, is defined as a basic relationship, and
piezoelectric material layers are periodically arranged so that (4P+2)th layer of the piezoelectric materials, adjacent to (4P+1)th layer, and (4P+3)th layer thereon each has an opposite relationship to the basic relationship, and (4P+4)th layer has the same relationship as the basic relationship.

2. The ultrasound transducer of claim 1, wherein a plurality of the piezoelectric material layers are in an electrically parallel connection each other mutually by connecting two electrodes each located at outermost side of two adjacent piezoelectric material layers.

3. The ultrasound transducer of claim 1, comprising a laminated piezoelectric material which comprises 3×m layers of piezoelectric materials, where m is an integer of 1 or more.

4. The ultrasound transducer of claim 1 wherein the de-matching layer comprises a tungsten carbide.

5. An ultrasound probe comprising the ultrasound transducer of claim 1 and
outputting an ultrasound by inputting an electrical signal into the laminated piezoelectric material through the electrodes.

6. The ultrasound probe of claim 5 comprising a plurality of the ultrasound transducers formed in array by forming electrodes arranged in array with a sequence at a predetermined interval on the surface of the piezoelectric material.

7. The ultrasound probe of claim 5 comprising a circuit board which connects with the electrodes electrically and has a predetermined wiring pattern, and the laminated piezoelectric material is integrally attached to the circuit board.

8. An ultrasound probe comprising the ultrasound transducer of claim 1, wherein the laminated piezoelectric material receives an ultrasound wave and changes it into an electrical signal, and outputs the electrical signal through the electrodes.

9. The ultrasound probe of claim 8, which outputs an ultrasound wave by inputting an electrical signal into the laminated piezoelectric material through the electrodes.

10. An ultrasound diagnostic imaging apparatus comprising the ultrasound probe of claim 8, a reception unit which receives the electrical signal, and an image processing unit which generates ultrasound image data based on the received electrical signal received by the reception unit.

11. An ultrasound transducer comprising:
a laminated piezoelectric material having n piezoelectric material layers, where n is an integer of 3 or more, each having an equal thickness, and electrodes between the piezoelectric material layers and on both end surfaces of the laminated piezoelectric material for input and output of an electrical signal, each of the piezoelectric material layers having a remanent polarization in a thickness direction, and a de-matching layer provided on an opposite surface side of a transmission of an ultrasound wave, wherein the de-matching layer has a larger acoustic impedance than the laminated piezoelectric material and reflects a vibration propagated from the laminated piezoelectric material to the de-matching layer side, wherein the ultrasound transducer resonates by a thickness stretch of the piezoelectric materials, a relationship between a direction of an electrical displacement by the direct piezoelectric effect or a direction of an electrical field of a piezoelectric material generated by a voltage applied to the electrodes and a direction of the remanent polarization in the (4P+1)th layer from the de-matching layer side, where P is 0 or a positive integer, is defined as a basic relationship, and piezoelectric materials are periodically arranged so that (eP+2)th layer of the piezoelectric materials adjacent to (8P+1)th layer has the same relationship as the basic relationship, (8P+3)th layer to (8P+6)th layer thereon each has an opposite relationship to the basic relationship, and (8P+7)th layer and (8P+8)th layer each has the same relationship as the basic relationship.

* * * * *